(12) United States Patent
Rojas et al.

(10) Patent No.: US 9,290,492 B2
(45) Date of Patent: Mar. 22, 2016

(54) SOLID FORMS OF ANTIBIOTICS

(75) Inventors: Hugo Morales Rojas, Morelos (MX);
Jorge Guillermo Domínguez Chávez,
Morelos (MX); Dea Herrera Ruiz,
Morelos (MX); Herbert Höpfl, Morelos
(MX); Juan Manuel Martínez Alejo,
Morelos (MX); **Juan Pablo Senosiain
Peláez**, Mexico City (MX)

(73) Assignee: Laboratorios Senosiain S.A. de C.V.,
Mexico City (MX)

( * ) Notice: Subject to any disclaimer, the term of this
patent is extended or adjusted under 35
U.S.C. 154(b) by 0 days.

(21) Appl. No.: 14/115,335

(22) PCT Filed: Apr. 27, 2012

(86) PCT No.: PCT/IB2012/052139
§ 371 (c)(1),
(2), (4) Date: Dec. 10, 2013

(87) PCT Pub. No.: WO2012/150537
PCT Pub. Date: Nov. 8, 2012

(65) Prior Publication Data
US 2014/0088116 A1    Mar. 27, 2014

(30) Foreign Application Priority Data
May 4, 2011 (MX) .................. MX/a/2011/004759

(51) Int. Cl.
*C07D 215/00*  (2006.01)
*A61K 31/47*   (2006.01)
*C07D 471/04*  (2006.01)
*C07D 215/56*  (2006.01)

(52) U.S. Cl.
CPC ............ *C07D 471/04* (2013.01); *C07D 215/56* (2013.01)

(58) Field of Classification Search
None
See application file for complete search history.

(56) References Cited

U.S. PATENT DOCUMENTS

| | | | |
|---|---|---|---|
| 6,610,327 | B1 | 8/2003 | Bosche et al. |
| 7,230,006 | B2 | 6/2007 | Reddy et al. |
| 8,207,339 | B2 | 6/2012 | Castellin et al. |
| 8,920,559 | B2 | 12/2014 | Childs et al. |

FOREIGN PATENT DOCUMENTS

ES  2127036        1/1999
WO  WO 2009136408 A1 * 11/2009

OTHER PUBLICATIONS

Pandit, N., "Introduction to the Pharmaceutical Sciences" Baltimore, Lippincott 2007, p. 19.*
Basavoju, Bostrom and Velaga, Pharmaceutical Cocrystal and Salts of Norfloxacin, Crystal Growth & Design, Oct. 13, 2006, vol. 6, No. 12, pp. 2699-2708, American Chemical Society, published on World Wide Web Internet.
International Search Report of Oct. 2, 2012, in English, for corresponding International Application No. PCT/IB2012/052139.

* cited by examiner

*Primary Examiner* — Heidi Reese
(74) *Attorney, Agent, or Firm* — Stephen S. Hodgson

(57) ABSTRACT

The invention relates to novel solid forms of fluoroquinolones, in particular to complex co-crystals and to solvates, hydrates and polymorphs thereof. These substances can be used to prepare a pharmaceutical composition containing same as an active ingredient, which can be used as an antibiotic. The compounds have a storage stability that is constant and above that of the salts or hydrates thereof.

27 Claims, 35 Drawing Sheets

SOLID FORMS OF ANTIBIOTICS

FIELD OF THE INVENTION

The present invention relates to novel solid forms of fluoroquinolones, particularly to complex co-crystals and solvates, hydrates and polymorphs thereof, and their use in the preparation of a pharmaceutical composition useful as an antibiotic.

BACKGROUND OF THE INVENTION

The present invention relates to novel solid forms (NSF) of fluoroquinolones, particularly to complex crystals, which have a consistent quality and improved physicochemical properties such as chemical and physical stability and higher dissolution rate.

The present invention describes co-crystals obtained from a fluoroquinolone salt and a neutral co-former, where both are solid at room temperature. For the present case we designate them as "complex co-crystals", which have improved physicochemical properties, such as increased solubility, dissolution rate, enhanced flow properties and stability.

For the present invention, the NSF are also called co-crystals, obtained by technical experimentation. The co-crystals are chemical entities with different physicochemical properties as compared to the salts or polymorphs of the active agent on which they are based on, because of the nature of intermolecular interactions between the molecule of matter and a second solid constituent, the latter hereinafter designated as coformer.

A co-crystal is a multicomponent crystal, in which the starting components are solid under ambient conditions and in their pure form, and in which two or more components of the co-crystal form aggregates that are characterized by being bound together by interactions—such as Van der Waals forces, π-stacking, hydrogen bonding or electrostatic interactions, but without forming covalent bonds. By employing crystal engineering techniques a new substance can be obtained with modified physicochemical properties that differ from the existing polymorphs, salts, hydrates and/or solvates. The exploration adjustable parameters are better, so the physical properties of the active principle with clinical relevance can be optimized.

The pharmaceutical co-crystals are co-crystals containing at least one therapeutic molecule and a pharmaceutically acceptable co-former. In these substances, such components coexist in a well-defined stoichiometric ratio between the active ingredient and the co-former. Co-crystals in solid form tend to be more stable than the existing solvates or hydrates.

Fluoroquinolones are a group of synthetic antimicrobial agents. Structurally, they consist of a heterocyclic derivative of 4-quinolone with a fluorine atom attached to C6, as shown in Scheme I, and several substituent groups R1, R2, R3 and R4 that may be, among others, hydrogen, alkyl chains, alkoxy groups, amino, cyclopropoxy and/or heteroaromatic rings such as piperazine, cinnoline and piridopiridine at position 7 (R2).

Scheme I. General structure of fluoroquinolones.

R1 may be H, an alkyl chain or a carboxyl;

R2 may be a heterocyclic amine such as pyridine, piperazine, piperidine, pirrolpiridine, pirrolpiperazina, cinnoline, morpholine, pyrrole, pyrrolidone;

R3 may be an H, an alkyl chain or an alkoxy;

R4 may be an H, an alkyl chain, carboxyl, cyclo propyl, indole ethanol, an alkyl chain or a linear carboxyl or attached to an alkoxy, which may or may not form a ring with R3.

The most representative fluoroquinolones are: ofloxacin, levofloxacin (S(-)enantiomer ofloxacin), enoxacin and pefloxacin, lomefloxacin, norfloxacin, ciprofloxacin, grepafloxacin (ciprofloxacin analog), sparfloxacin, tosufloxacino, gatifloxacin, trovafloxacin, clinafloxacin, sitafloxacin, moxifloxacin and gemifloxacin. The present invention develops a method of obtaining co-crystals or other solid forms starting from the salts of some of these fluoroquinolones, such as moxifloxacin, levofloxacin or ciprofloxacin.

Moxifloxacin is a fourth-generation antibiotic of the fluoroquinolone group. Its structural formula is shown in Scheme II.

Scheme II. Moxifloxacin structure

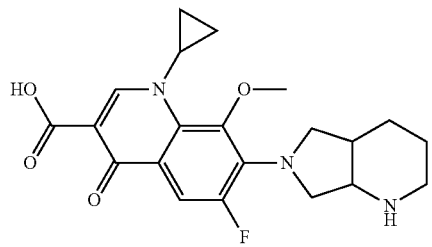

In commercial pharmaceutical preparations moxifloxacin is in the form of hydrochloride salt, which is water soluble, has an absolute bioavailability of 86 to 92%, has a plasmatic protein binding of from 30% to 50%, has a half-life between 11.5 and 15.6 hours (single dose) and its excretion is via the liver [Zhanel G G et al. "A critical review of the fluoroquinolones", Drugs, 62 (1), p. 13-59 (2002)]. This fluoroquinolone is active against gram-positive and gram-negative bacteria. It is administered orally or parenterally in a single dose of 400 mg once daily and has a good pharmacokinetic profile. Approximately 45% of an oral or intravenous dose of moxifloxacin is excreted as the unchanged drug (~20% in urine and ~25% in feces) [Rodvold K A et al. "Pharmacokinetics and pharmacodynamics of fluoroquinolones", Pharmacotherapy, 21 (10 Pt 2), pp. 233S-252S (2001)].

Levofloxacin is a broad spectrum antibiotic which consists of the S(-) isomer of ofloxacin (Scheme III). Levofloxacin hemihydrate is used in commercial pharmaceutical compositions. It has a bioavailability of 99%, it has a plasmatic protein binding of from 24% to 38%, it has a half-life between 6 and 8 hours (single dose), it is administered at a dose of from 250 mg to 500 mg once or twice a day and is excreted via urine. [Pharmaceutical Press. Martindale: The complete Drug Reference. Levofloxacin. 2011. Accessed http://www.medicinescomplete.com. Apr. 12, 2011].

Scheme III. Levofloxacin structure

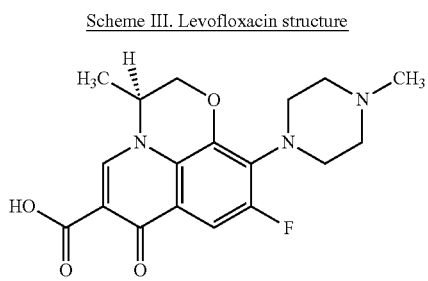 [SMILES: C[C@H]1COc2c(N3CCN(C)CC3)c(F)cc3c(=O)c(C(=O)O)cn1c23]

Ciprofloxacin is a broad spectrum antibiotic that belongs to the family of antibiotics called fluoroquinolones, and its chemical formula is shown in Scheme IV. It is effective against gram-positive and gram-negative bacteria, it functions by inhibiting the DNA gyrase, a type II topoisomerase which is an enzyme required to separate the replicated DNA, inhibiting cellular division. Pharmaceutical compositions employ ciprofloxacin hydrochloride, a salt which is soluble in water and alcohol. In a 2.5% water solution it has a pH of from 3.5 to 4.5. It must be protected from light. Ciprofloxacin is rapidly and well absorbed from the gastrointestinal tract. The oral bioavailability is from 70% to 80%, the absorption of ciprofloxacin tablets may be delayed by the presence of food, but not substantially affected as a whole; it has a plasma protein binding of from 20% to 40%, it has a half-life of from 3 to 5 hours (single dose) and is excreted through kidney route. [Pharmaceutical Press. Martindale: The complete Drug Reference. Ciprofloxacin. 2011. Accessed http://www.medicinescomplete.com. Apr. 12, 2011].

Scheme IV. Ciprofloxacin structure

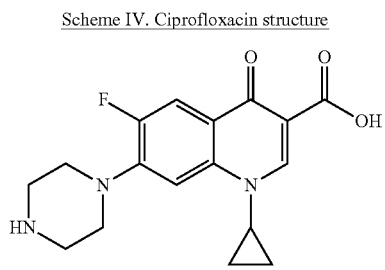

Adverse Effects

In general, fluoroquinolones are well tolerated, however, the most common side effects are: effects on the articular growth, erosion of the cartilage in growth, especially in weight-bearing joints. For this reason fluoroquinolones should not be administered to children and adolescents under 18 years old. The most serious adverse effect is particularly of cardiologic type as the duration of the QT interval of the electrocardiogram might be affected. If this interval is abnormally prolonged, may generate arrhythmias.

Interactions with Other Medicaments

Fluoroquinolones enhance the effect of anticoagulants and may enhance the hypoglycemic effect of sulfonylureas. Furthermore, aluminum salts (including sucralfate), magnesium, calcium, iron and zinc, significantly reduce the bioavailability of fluoroquinolones by non-absorbable chelators formation.

BACKGROUND

Document WO2009/136408 (Institute of Life Sciences), describes the preparation of co-crystals from second generation quinolones, ciprofloxacin and norfloxacin, specifically in its basic form. The aforementioned document comprises co-crystals of ciprofloxacin with co-formers eugenol, ferulic acid, isoferulic acid, citric acid or tartaric acid. The norfloxacin co-crystal is presented with co-formers like eugenol, ferulic acid, isoferulic acid, caffeine, citric acid, glutamic acid, vanillin, phenylalanine or resveratrol.

The present invention, unlike the aforementioned co-crystals in WO2009/136408, comprises "complex" co-crystals which are obtained from salts of a fluoroquinolone such as moxifloxacin or ciprofloxacin or levofloxacin, and which are not in their neutral form. The co-crystals of the present invention are obtained with co-formers of the kind of glycolic acid, 3-hydroxybenzoic acid, 4-hydroxybenzoic acid, 2,4-dihydroxybenzoic acid, 2,5-dihydroxybenzoic acid, 3,4-dihydroxybenzoic acid, 3,5-dihydroxybenzoic acid, gallic acid, DL-malic acid, tartaric acid, cathecol, resorcinol, 4-aminobenzoic acid and 4-hydroxybenzamide. Such co-formers include one or more hydroxyl groups and/or carboxylic acid(s) that form an aggregate with fluoroquinolone hydrochloride, which may be selected without limitation from moxifloxacin, ciprofloxacin or levofloxacin.

Document WO2004091619 discloses a process for obtaining the crystalline form III of moxifloxacin hydrochloride or monohydrate. Said compound is obtained by a process of azeotropic reflux of moxifloxacin monohydrochloride, in a selection of organic solvents with subsequent alcohol washes for its purification and separation. The obtained crystalline form III is stable and can be used in the manufacture of a solid pharmaceutical composition for use as an antibiotic. Unlike document WO2004091619, the present invention comprises co-crystals of moxifloxacin hydrochloride; these co-crystals have better physicochemical properties, or process properties, such as improved solubility, dissolution rate, bioavailability, stability and/or flow properties.

Document WO2005089375 discloses a process for obtaining co-crystals of API through ultrasound and crystallization. For obtaining such co-crystals it is necessary to prepare the components which will form the co-crystal, which are prepared separately in either solutions or emulsions, on one hand the active ingredient and on the other the co-former; mixtures are saturated in a solvent or solvent mixture, then the preparations are combined in at least one environment having a temperature of 1° C. and are subjected to ultrasound, which will eventually form co-crystals.

Unlike this process, the present invention is specific for obtaining co-crystals of fluoroquinolones mainly by the method of crystallization from solution using an excess of co-former, or by the methods of solid phase transformation (slurry) and/or grinding, with the use of minimum solvent amount and environmental conditions that do not involve taking it to freezing point. This obtention process lowers the equipment operation costs to obtain co-crystals and has a minimum impact on the environment, because basically no organic solvents are used.

JUSTIFICATION OF THE INVENTION

The rational use of antibiotics aims to get the most benefit for people who use them, limiting the development of resistant organisms and minimizing economic costs. Hence the importance of relying on a drug that produces the same therapeutic effect with lower doses and thereby decreasing side effects, achieving greater adherence to the treatment and consequently reducing the creation of resistant strains.

Moxifloxacin, levofloxacin and ciprofloxacin are broad spectrum antibiotics of delicate use, so that there is need of having complex co-crystals that increase the activity and allow for a lower dose to the patient.

In the prior art there is no information about the formation of complex co-crystals of moxifloxacin, ciprofloxacin or levofloxacin salts. During the process of obtaining co-crystals one may conceive of a lot of combinations with potential co-formers. However, not all combinations produce a co-crystal or a solid stable form. In addition, the co-crystals that unexpectedly may be obtained, may or may not have better rheological properties, of solubility or physicochemical properties.

Although there is a good understanding of the physicochemical of the components of a co-crystal, it is practically impossible their elucidation a priori, as the interactions that determine their structure are relatively weak and the number of degrees of freedom of the optimization problem is immeasurable. In the case of salts, their formation is not as difficult as that of the co-crystals, however, there is not a reliable way to determine a priori whether their physicochemical characteristics such as solubility, chemical and physical stability will be suitable for a pharmaceutical composition. For these reasons, the new solid forms disclosed in this document are not obvious to a person skilled in the art.

SUMMARY OF THE INVENTION

The present invention provides several undisclosed compounds of moxifloxacin, ciprofloxacin and other fluoroquinolones, which are identified as complex co-crystals formed from a salt of the antibiotic and a neutral co-former. These co-crystals have enhanced physicochemical and biopharmaceutical properties, which confer advantages for the preparation of pharmaceutical compositions, such as improved bioavailability, improved solubility, dissolution rate, enhanced processability of the drug and/or enhanced pharmacokinetic properties, and consequently, fewer side effects.

BRIEF DESCRIPTION OF THE DRAWINGS

FIGS. 1-22 illustrate the results of the characterization of the moxifloxacin co-crystals obtained in the present invention.

FIG. 1. X-ray powder diffraction pattern of the co-crystal of Moxifloxacin HCl with 4-hydroxybenzoic acid.

FIG. 2. DSC-TGA thermal analysis of the co-crystal of Moxifloxacin HCl with 4-hydroxybenzoic acid.

FIG. 3. TF-Infrared spectrum of the co-crystal of Moxifloxacin HCl with 4-hydroxybenzoic acid.

FIG. 4. CP-MAS $^{13}$C NMR spectrum of a) moxifloxacin, b) 1 to 1 physical mixture of moxifloxacin and 4-hydroxybenzoic acid, and c) moxifloxacin co-crystal with 4-hydroxybenzoic acid.

FIG. 5. Crystalline structure of the co-crystal of moxifloxacin HCl with 4-hydroxybenzoic acid.

FIG. 7. DSC-TGA thermal analysis of the co-crystal of moxifloxacin HCl with 2,5-dihydroxybenzoic acid.

FIG. 8. TF-Infrared spectrum of the co-crystal of moxifloxacin HCl with 2,5-dihydroxybenzoic acid.

FIG. 9. Crystalline structure of the co-crystal with moxifloxacin HCl co-crystal and 2,5-dihydroxybenzoic acid.

FIG. 10. X-ray powder diffraction pattern of the co-crystal with moxifloxacin HCl and 3-hydroxybenzoic acid.

FIG. 11. X-ray powder diffraction pattern of the co-crystal with moxifloxacin HCl and 2,4-dihydroxybenzoic acid.

FIG. 13. X-ray powder diffraction pattern of the co-crystal of moxifloxacin HCl monohydrate with 3,5-dihydroxybenzoic acid.

FIG. 14. X-ray powder diffraction pattern of the co-crystal of moxifloxacin HCl with gallic acid.

FIG. 15. X-ray powder diffraction pattern of the co-crystal of Moxifloxacin HCl with cathecol.

FIG. 16. X-ray powder diffraction pattern of the co-crystal of moxifloxacin HCl with resorcinol.

FIG. 17. X-ray powder diffraction pattern of the co-crystal of moxifloxacin HCl with glycolic acid.

FIG. 18. X-ray powder diffraction pattern of the co-crystal of moxifloxacin HCl with DL-malic acid.

FIG. 19. X-ray powder diffraction pattern of the co-crystal of moxifloxacin HCl with D-tartaric acid.

FIG. 20. X-ray powder diffraction pattern of the co-crystal of moxifloxacin HCl with 4-hydroxybenzamide.

FIG. 21. X-ray powder diffraction pattern of the co-crystal of moxifloxacin HCl with 4-aminobenzoic acid.

FIG. 22. X-ray powder diffraction pattern of the co-crystal of moxifloxacin HCl with 4-hydroxybenzyl alcohol.

FIG. 23. X-ray powder diffraction pattern of the co-crystal of ciprofloxacin HCl with 4-hydroxybenzoic acid.

FIG. 24. X-ray powder diffraction pattern of the co-crystal of ciprofloxacin HCl with 3-hydroxybenzoic acid.

FIG. 25. X-ray powder diffraction pattern of the co-crystal of ciprofloxacin HCl with 2,3-dihydroxybenzoic acid.

FIG. 26. X-ray powder diffraction pattern of the co-crystal of ciprofloxacin HCl with 2,4-dihydroxybenzoic acid.

FIG. 27. X-ray powder diffraction pattern of the co-crystal of ciprofloxacin HCl with 2,5-dihydroxybenzoic acid.

FIG. 28. X-ray powder diffraction pattern of the co-crystal of ciprofloxacin HCl co-crystal with 3,4-dihydroxybenzoic acid.

FIG. 29. X-ray powder diffraction pattern of the co-crystal of ciprofloxacin HCl with 3,5-dihydroxybenzoic acid.

FIG. 30. X-ray powder diffraction pattern of the co-crystal of ciprofloxacin HCl with cathecol.

FIG. 31. X-ray powder diffraction pattern of the co-crystal of ciprofloxacin HCl with resorcinol.

FIG. 32. X-ray powder diffraction pattern of the co-crystal of ciprofloxacin HCl with hydroquinone.

DETAILED DESCRIPTION OF THE INVENTION

Figure 1:
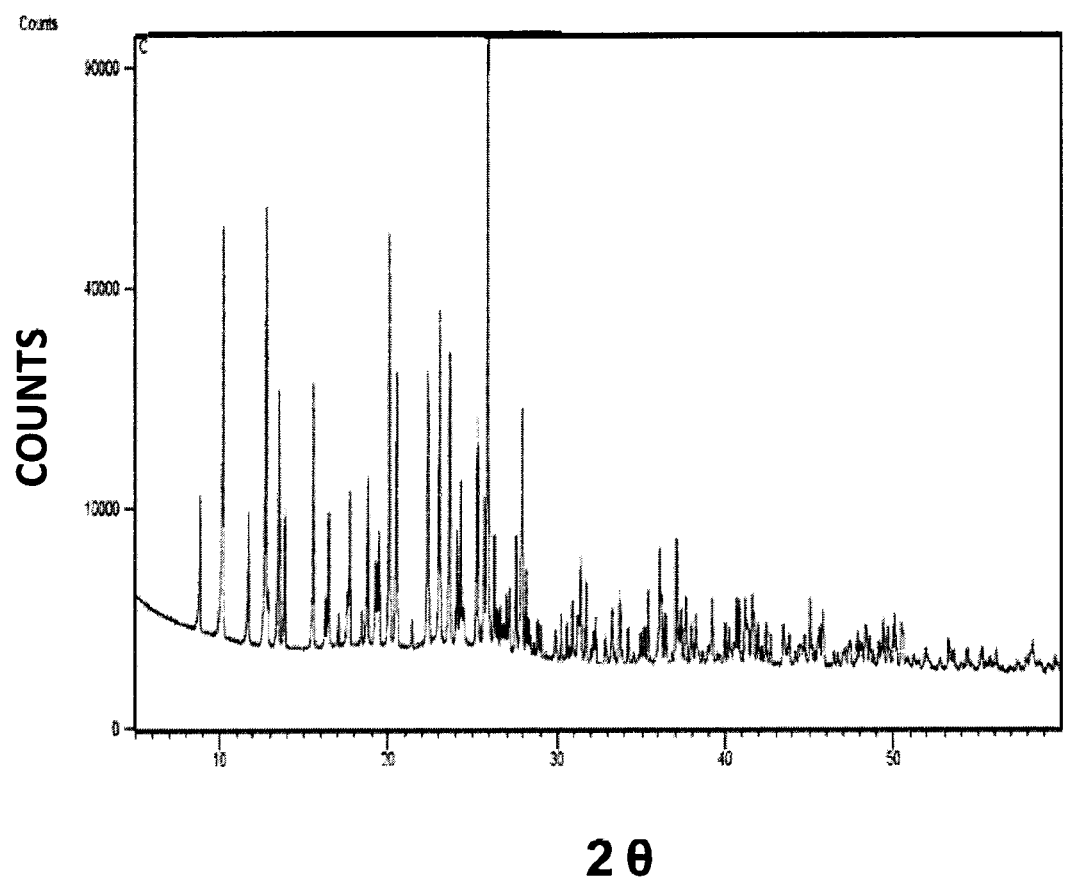

One of the challenges faced by the development of the present invention was to obtain a stable compound of fluoroquinolone, with high purity, with physicochemical properties suitable for preparing a pharmaceutical composition and which improves the existing forms in terms of stability, solubility and/or dissolution rate. Due to the complexity of the interactions in a solid structure, the final structure and thus the properties of the new solid forms are impossible to predict theoretically, so that a number of experiments had to be carried out to find the compounds described herein.

The complex co-crystals of the present invention, in the preferred embodiment, are formed from fluoroquinolone-halide salt and neutral co-former, both being solids at room temperature. The NSF obtained from the combination of these solids, consist of an aggregate in which the components of the fluoroquinolone salt and the neutral co-former molecule interact through hydrogen bonding, Van der Waals or electrostatic interactions. The new solid form obtained in the present invention offer the advantage of generating solid active ingredients with improved physicochemical properties, such as improved solubility, stability or easy-flowing properties.

The present invention started from a fluoroquinolone salt which may be, for example, ciprofloxacin or moxifloxacin in its hydrochloride form.

Moxifloxacin hydrochloride was reacted with a variety of possible co-formers in the presence of solvents such as tetrahydrofuran (THF), methanol (MeOH), dimethyl sulfoxide (DMSO), dimethylformamide (DMF), acetone, acetonitrile or water. In the preferred embodiment saturated solutions of the respective co-formers were prepared, to which small amounts of solid moxifloxacin hydrochloride were added under constant agitation. The added solid is dissolved and additions are interrupted due to the appearance of a new insoluble solid form in the dissolution medium. From these reactions several possible combinations among moxifloxacin, coformer and solvent were carried out. The product of these reactions was characterized by X-ray powder diffraction assay. This test showed that NSF were generated either as solvates, hydrates and co-crystals. From the results of these tests it was concluded that the formation of co-crystals is neither simple nor predictable. The new solid phases that form an aggregate with moxifloxacin hydrochloride can be obtained by several methods such as grinding, the solid phase transformation (slurry) and/or crystallization of saturated solutions.

In the present invention was carried out with the following co-formers, among others: aliphatic carboxylic acids, aromatic carboxylic acids, hydroxybenzoic aromatic acids, hydroxycarboxylic acids, polyols (aromatic polyols), benzamide derivative, benzyl alcohol, dextrins, amino acid derivatives, disaccharides, polysaccharides, monosaccharides and/or polyphenols such as gallic acid (known as gallates), flavones, cinnamic acid and its derivatives such as quercetin, catechin, epigallocatechin and/or resveratrol. In the early tests of the present invention new solid forms (NSF) were obtained, which were stable with co-formers such as glycolic acid, 3-hydroxybenzoic and 4-hydroxybenzoic acid. These NSF obtained correspond to compounds wherein the neutral co-former has a hydroxyl group and a carboxylic acid, some of them also contain a phenyl as part of their structure.

Additionally, and in order to define the structural diversity of the co-formers that generate co-crystals, other reactions were carried out, now with hydroxycarboxylic acids and aromatic and aliphatic dicarboxylic acids such as benzoic acid, phthalic, isophthalic, terephthalic, and trans-cinnamic, which did not generate a NSF as product. Other reactions were performed with aromatic monocarboxylic acids with two or three hydroxy groups, such as vanillic acid, 2,4-dihydroxybenzoic acid, 2,5-dihydroxybenzoic acid, 3,4-dihydroxybenzoic, 3,5-dihydroxybenzoic acid and gallic acid. NSF were obtained with these co-formers, with the exception of vanillic acid.

In order to determine whether the replacement of a carboxylic acid instead an amide group in the 4-hydroxybenzoic acid and salicylic acid influenced the obtention of NSF, the corresponding benzamides (4-hydroxybenzamide and salicylamide) were examined. Also, 4-aminobenzoic acid and 4-hydroxybenzyl alcohol were tested. Similarly, analogs of nicotinamide and isonicotinamide were used, in which the amino group was replaced by the carboxylic group, generating the respective nicotinic and isonicotinic acids. Additionally, picolinic acid was included to complete the study on this type of compounds. The study also included the 2-hydroxynicotinic and cathecol, in order to explore the need of the phenyl group and the carboxylic acid in the structure of the co-formers. Resorcinol was used additionally as co-former, performing crystallization in saturated solution in methanol.

When working with aliphatic chain compounds, NSF were expected to be obtained by using dicarboxylic acids such as fumaric acid, adipic acid and pimelic acid, as stated by S. L. Childs et. al. [J. Am Chem Soc 2004, 126, pp. 13335]. As a result of working with aliphatic compounds, NSF were obtained with glycolic acid but not with the dicarboxylic acids. Other aliphatic carboxylic acids were tested, expecting for NSF formation, however, the novel forms were neither obtained with lactic acid nor glycine. For aliphatic polyols xylitol and L-ascorbic acid, in both DMSO and DMF, NSF were not obtained. NSF were obtained with malic acid and D-tartaric acid, again reflecting that the formation of NSF is not predictable.

Likewise and in order to determine the NSF formation with other molecules containing other types of donors for hydrogen bonding and aside from terminal carboxylic and hydroxyl groups, amino acids such as L-aspartic acid and L-glutamine were tested, as well as polyols such as cathecol, xylitol and ascorbic acid. The result was the formation of NSF only with cathecol, but not with xylitol or ascorbic acid.

Based on the results obtained for moxifloxacin hydrochloride, the ciprofloxacin hydrochloride salt was tested, and in this case it was reacted with a limited range of neutral co-formers, specifically those containing aromatic hydroxycarboxylic groups and aromatic diols in the presence of solvents such as tetrahydrofuran (THF), methanol (MeOH), dimethyl sulfoxide (DMSO), dimethylformamide (DMF), acetone, acetonitrile or water. In the preferred embodiment NSF were obtained in combination with the co-formers 3-hydroxybenzoic acid, 4-hydroxybenzoic acid, 2,5-dihydroxybenzoic acid, 3,4-dihydroxybenzoic acid, 3,5-dihydroxybenzoic acid, 2,4-dihydroxybenzoic acid, or 2,4-dihydroxybenzoic acid. Within this group NSF were not obtained when using 2-hydroxybenzoic acid or 2,6-dihydroxybenzoic in combination with ciprofloxacin hydrochloride. Additionally, NSF were generated from the combination with cathecol, resorcinol or hydroquinone.

Results of the Crystallization of Saturated Solutions for Obtaining NSF

Crystallization experiments with aromatic carboxylic acids, such as phthalic acid and terephthalic acid in MeOH and DMSO respectively, showed by means of the X-ray powder diffraction analysis that in both cases the solid obtained by the method of crystallization from saturated solutions corresponds exactly to moxifloxacin HCl, which means that no NSF was generated. Similar results were obtained for the trans-cinnamic acid, in which case the reactions were carried out with MeOH and DMSO.

Crystallization experiments with nicotinic acid, isonicotinic, picolinic acid and 2-hydroxynicotinic acid showed diffraction patterns similar to moxifloxacin HCl and its corresponding hidrosolvate. These obtained results ruled out the formation of NSF by the crystallization of the solutions with these coformers. These tests demonstrate that the crystallization reactions to form co-crystals are impossible to predict.

Figure 6A:
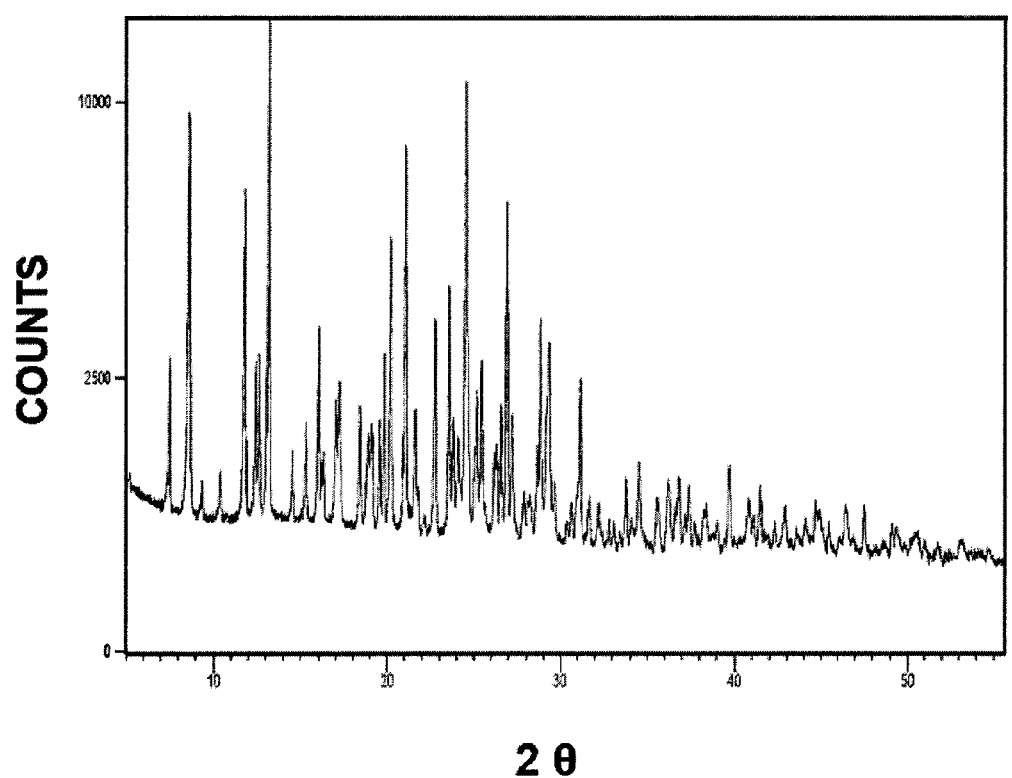
FIG. 6A. X-ray powder diffraction pattern of the co-crystal of moxifloxacin HCl with anhydrous 2,5-dihydroxybenzoic acid.
Figure 6B:
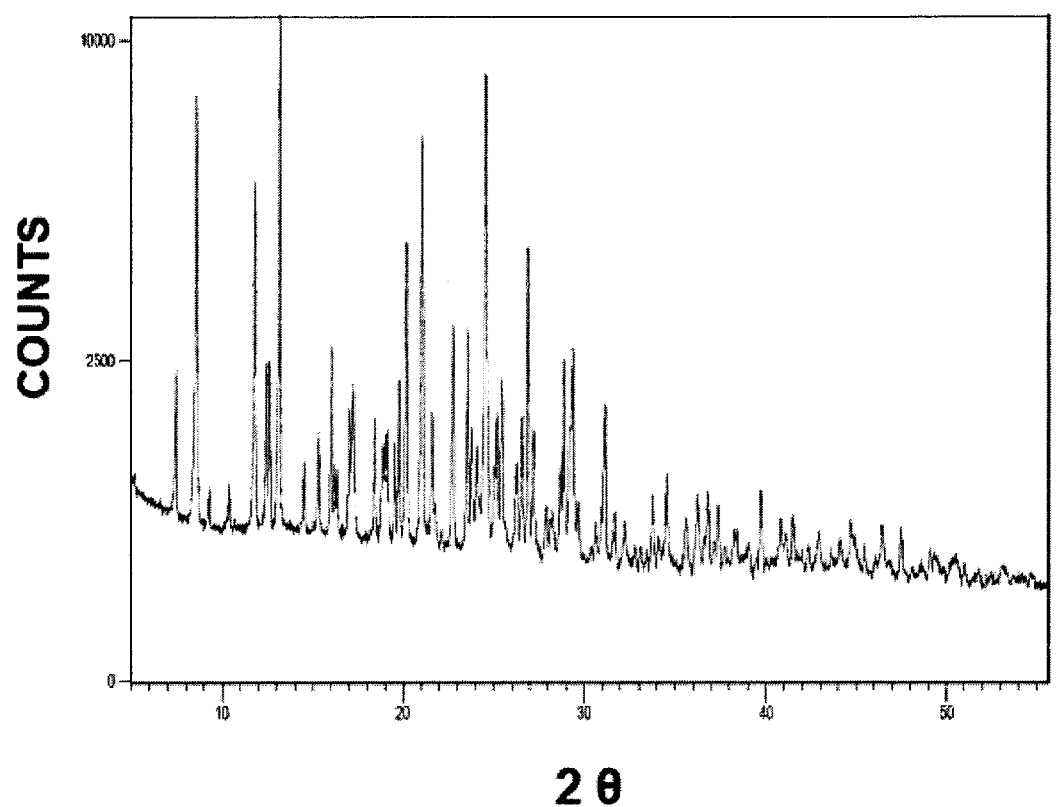
FIG. 6B. X-ray powder diffraction pattern of the co-crystal of moxifloxacin HCl with hydrated 2,5-dihydroxybenzoic acid.
Figure 6C:
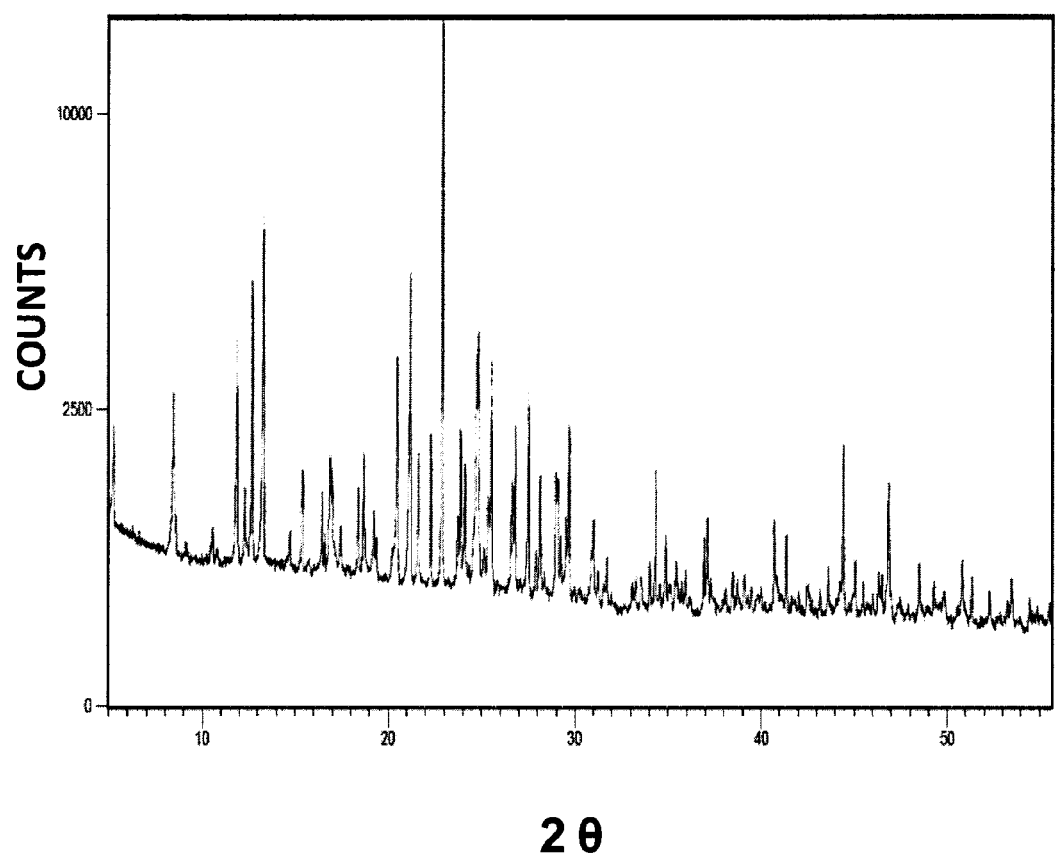
FIG. 6C. X-ray powder diffraction pattern of the co-crystal of moxifloxacin HCl with 2,5-dihydroxybenzoic acid solvate MeOH.
Figure 10:
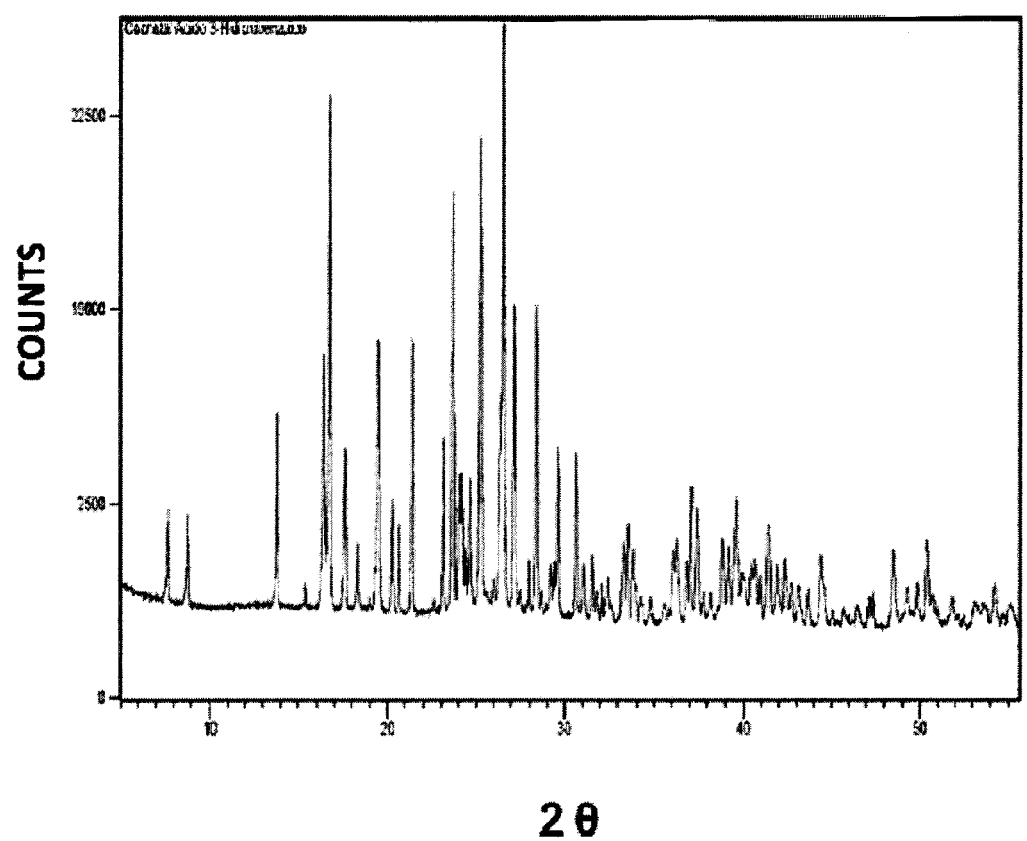
Figure 11:
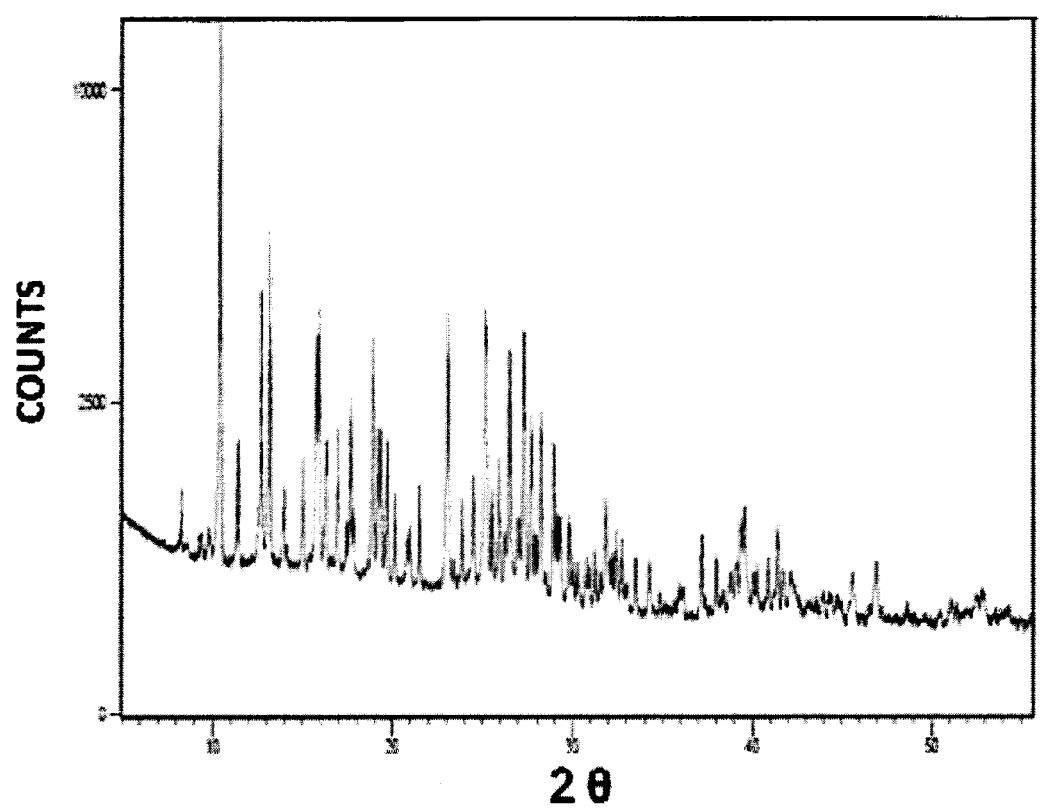
Figure 12A:
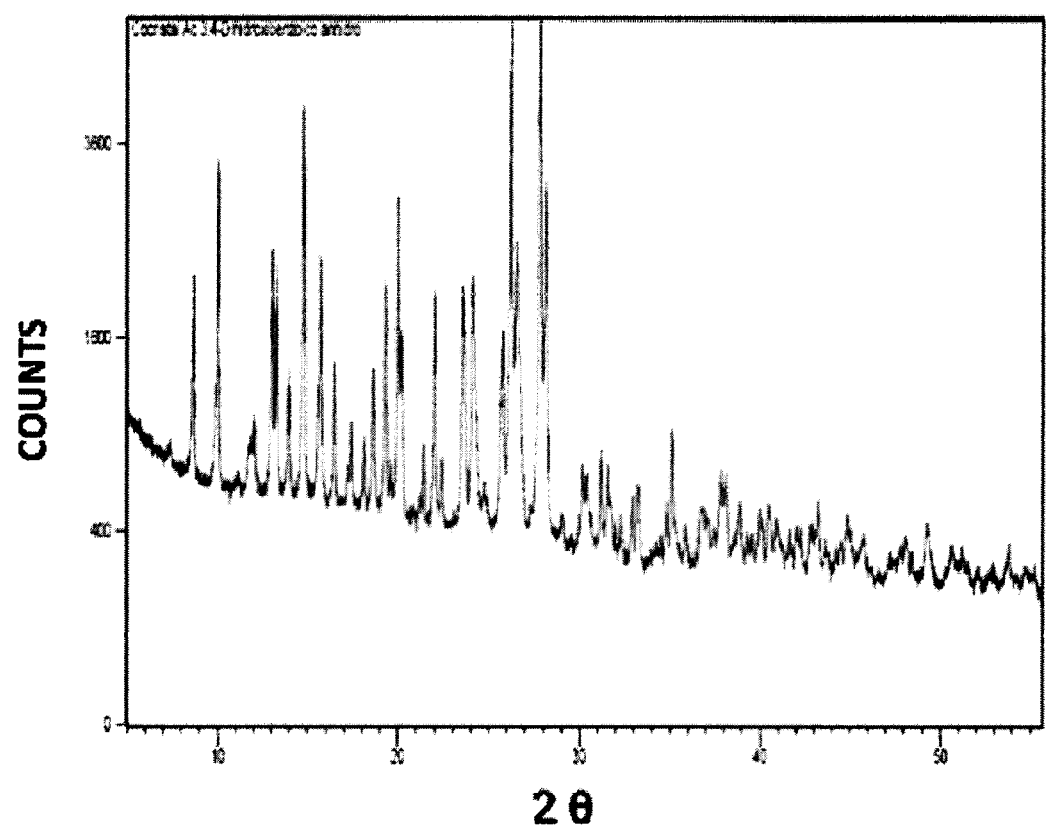
FIG. 12A. X-ray powder diffraction pattern of the co-crystal of moxifloxacin HCl with 3,4-dihydroxybenzoic acid anhydride.
Figure 12B:
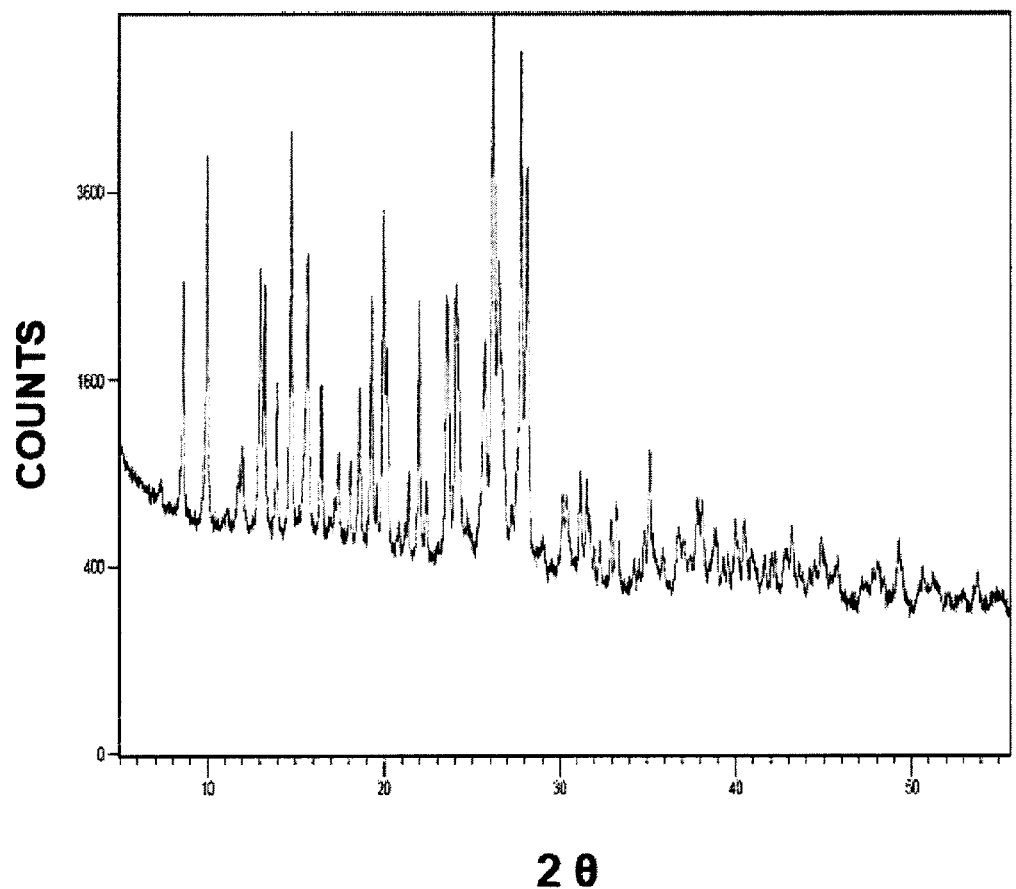
FIG. 12B. X-ray powder diffraction pattern of the co-crystal of moxifloxacin HCl with 3,4-dihydroxybenzoic acid sesquihydrate.
Figure 13:
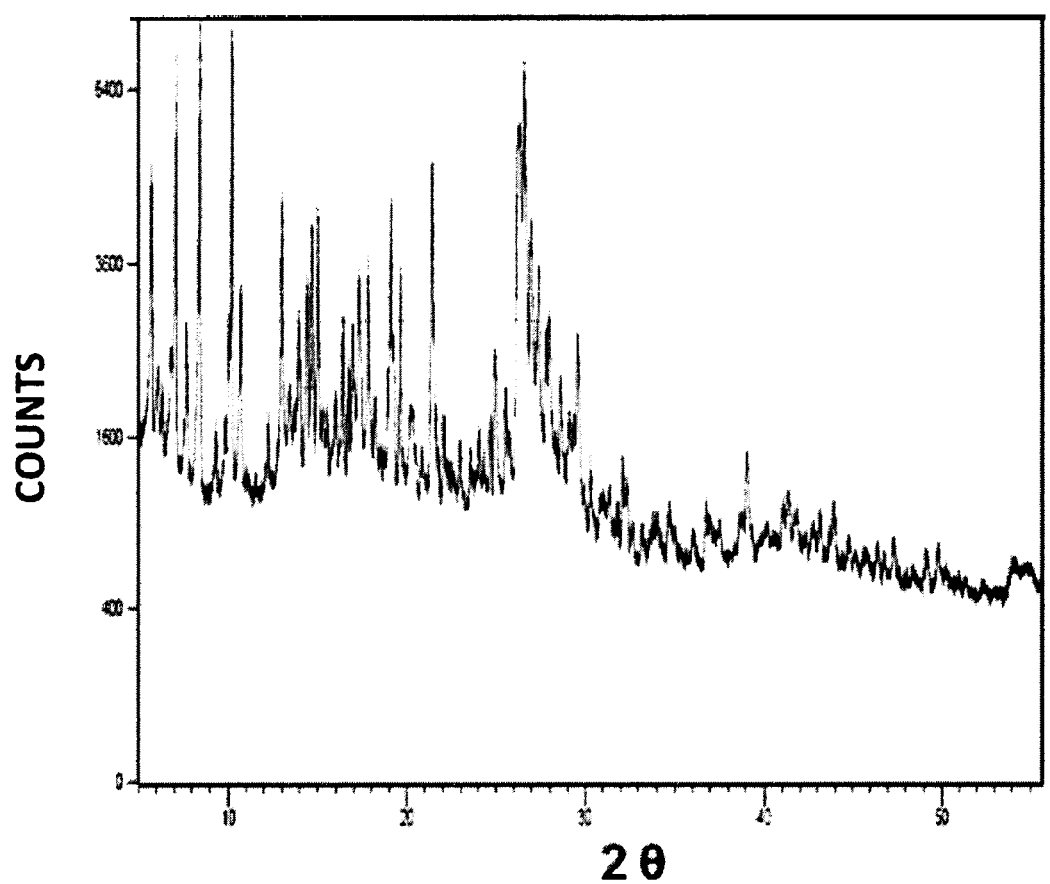

Crystallization processes performed with hydroxybenzoic acids gave different results, for example for crystallization of saturated solutions of 4-hydroxybenzoic acid in methanol resulted in a new phase, as shown in FIG. 1. Similarly using methanol or THF, NSF were obtained with the co-formers 3-hydroxybenzoic acid (FIG. 10), 2,4-dihydroxybenzoic acid (FIG. 11), 2,5-dihydroxybenzoic acid (FIGS. 6A, 6B and 6C), 3,4-hydroxybenzoic acid (FIGS. 12A and 12B) and 3,5-hydroxybenzoic acid (FIG. 13).

Figure 2:
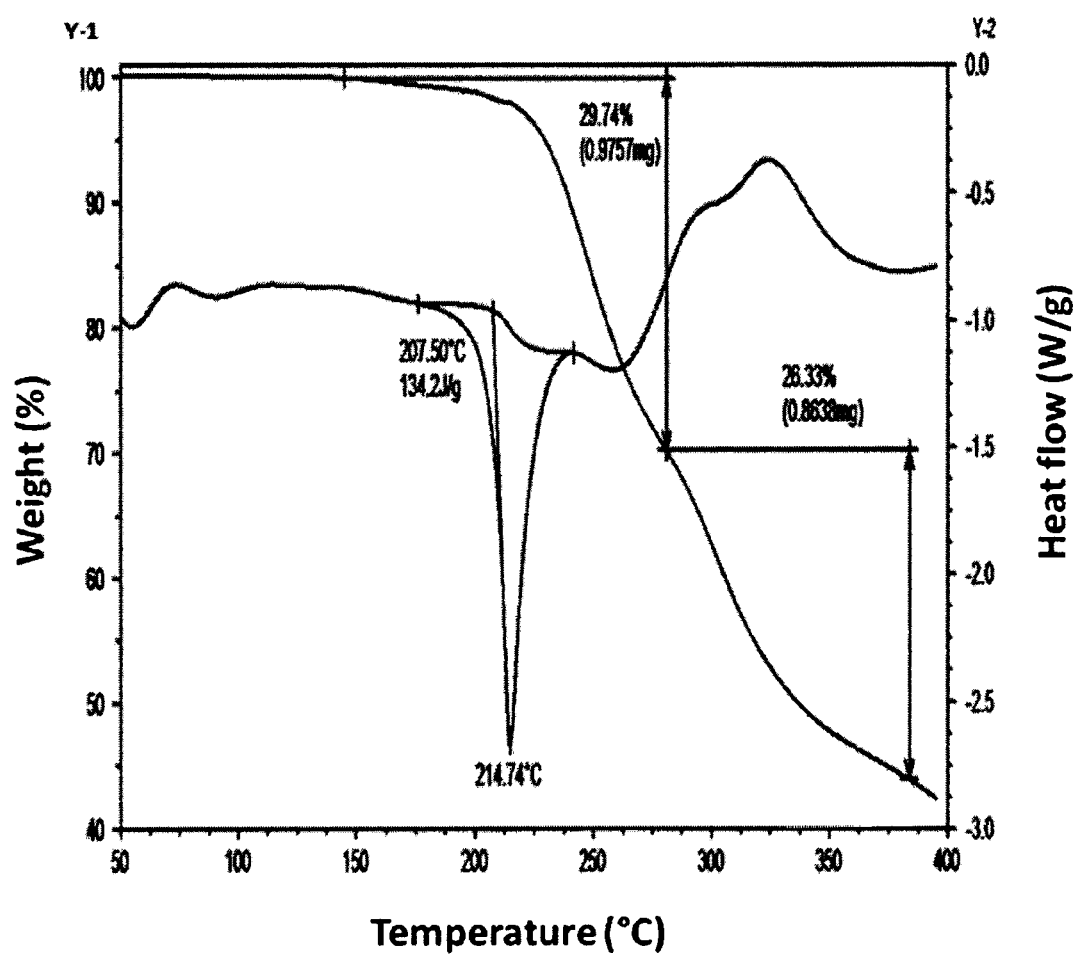
Figure 3:
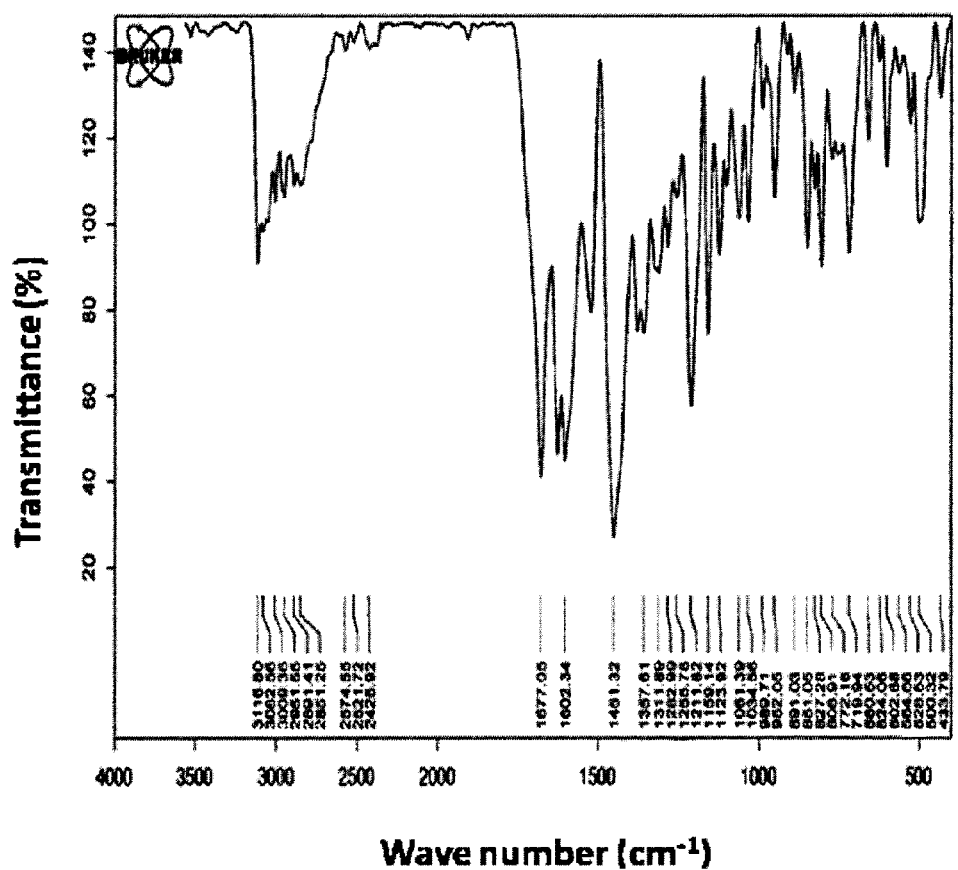
Figure 4:
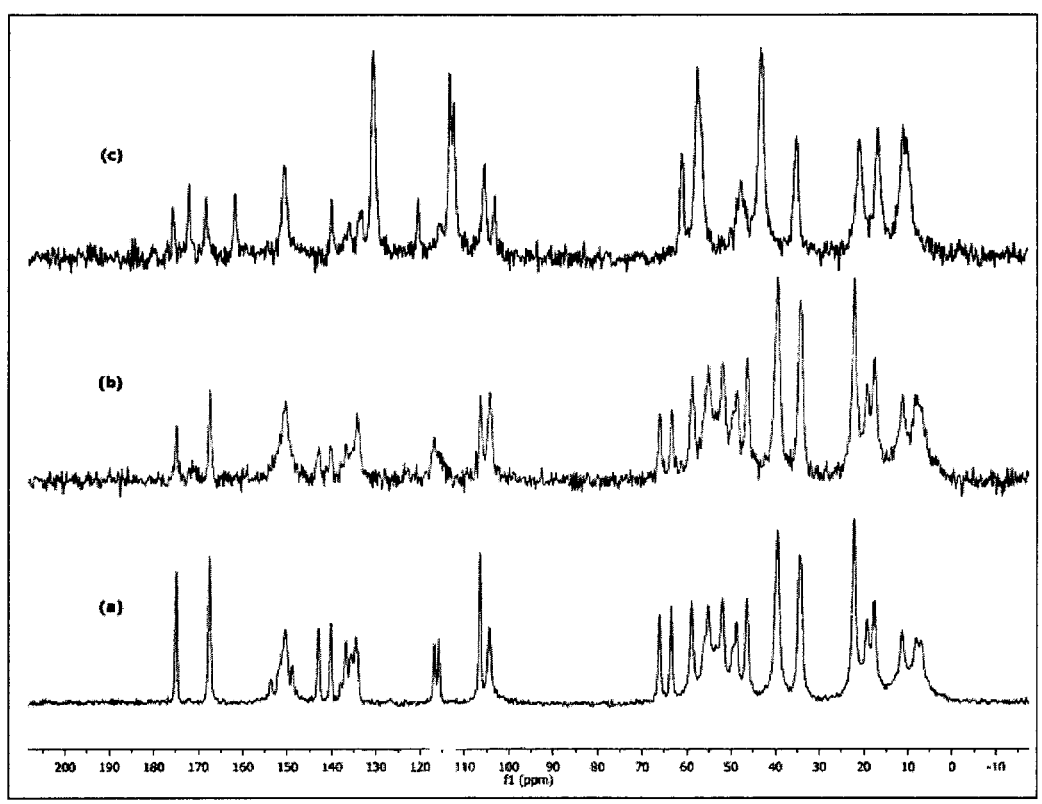

From the reactions between moxifloxacin HCl and 4-hydroxybenzoic acid, the formation of stable co-crystals was obtained. This was confirmed by X-ray Powder Diffraction (XRD) analysis, differential scanning calorimetry/thermogravimetric analysis (DSC/TGA), and infrared spectrum (FT-IR), as illustrated in the annexed figures. FIG. 3 shows the X-ray powder diffraction pattern of the co-crystal of moxifloxacin HCl with 4-hydroxybenzoic acid. FIG. 2 shows a DSC-TGA thermal analysis of the co-crystal of moxifloxacin HCl with 4-hydroxybenzoic acid. FIG. 4 shows the nuclear magnetic resonance spectrum (NMR) of the $^{13}$C core in solid-state ($^{13}$C CP-MAS NMR) of: a) moxifloxacin NSF; b) the physical mixture in the molar ratio 1 to 1 of moxifloxacin HCl/4-hydroxybenzoic acid; and c) moxifloxacin NSF with 4-hydroxybenzoic acid.

Figure 5:
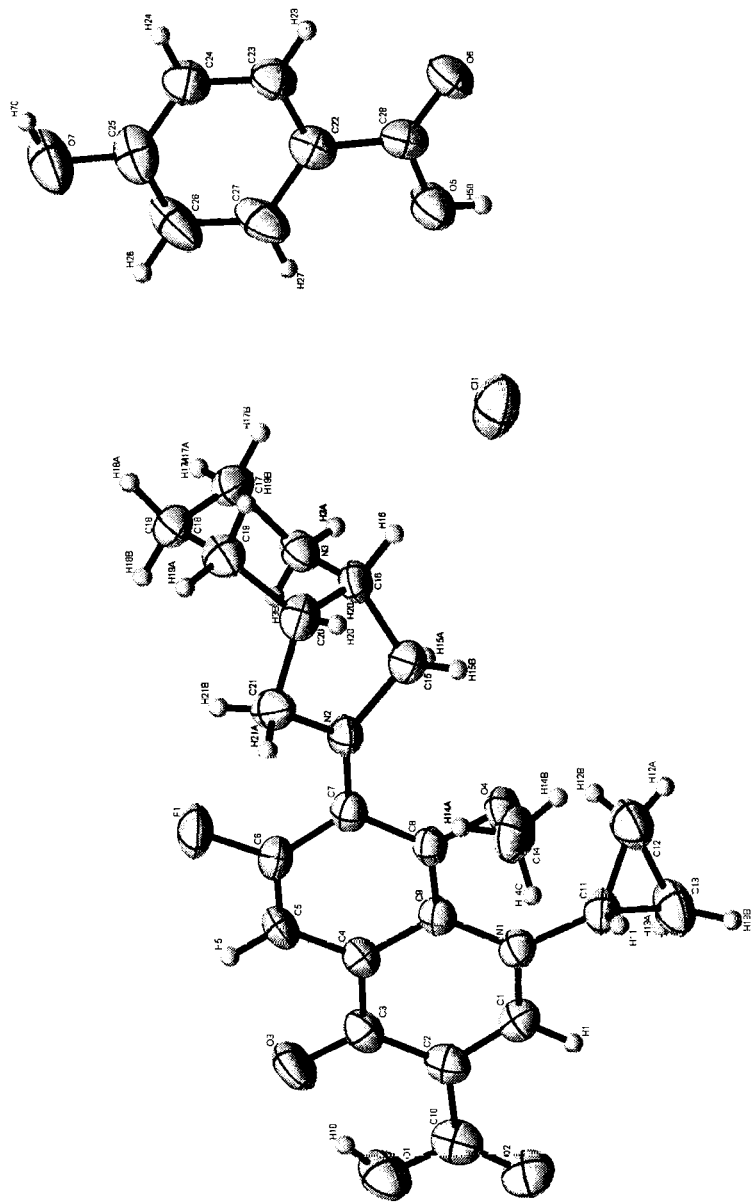

FIG. 5 shows the asymmetric unit of the crystalline structure of moxifloxacin HCl co-crystal with 4-hydroxybenzoic acid, obtained by X-ray diffraction of the monocrystal.

Figure 7:
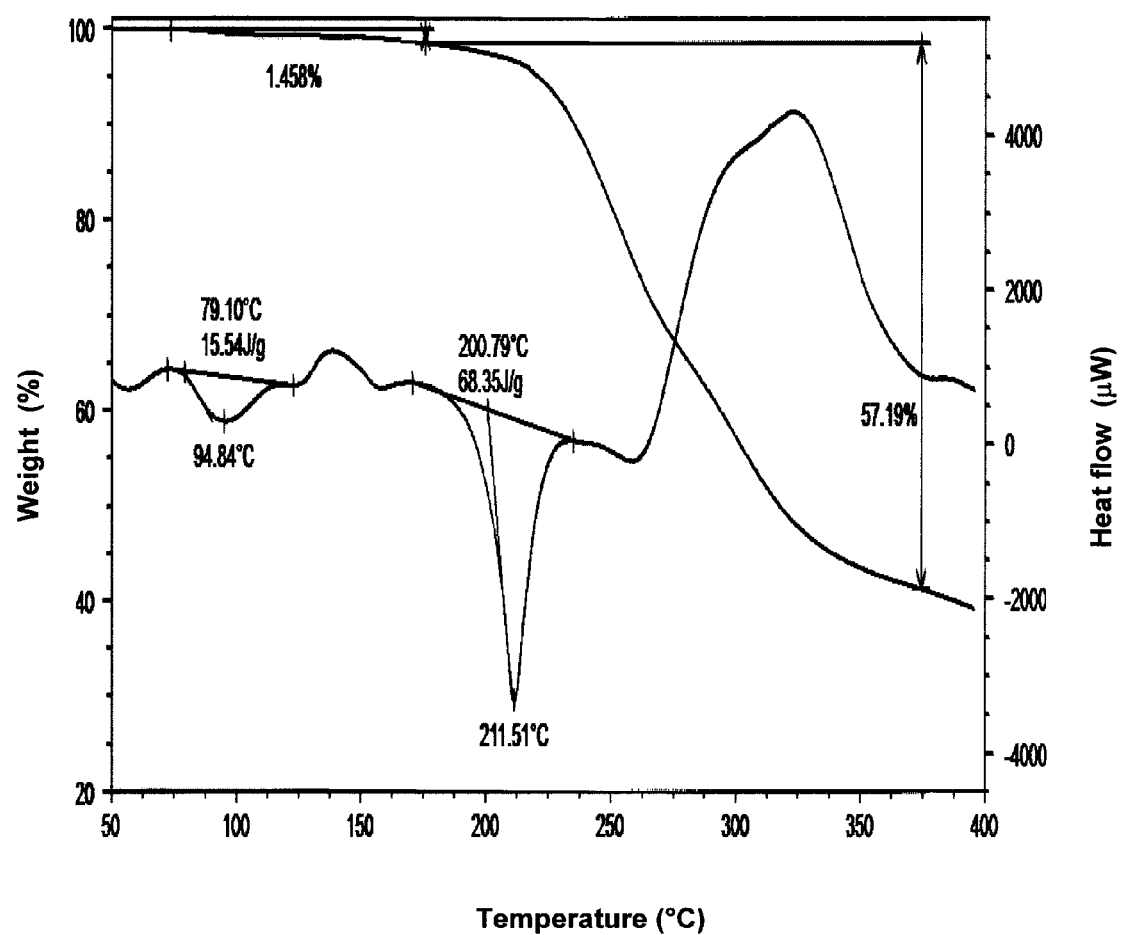
Figure 8:
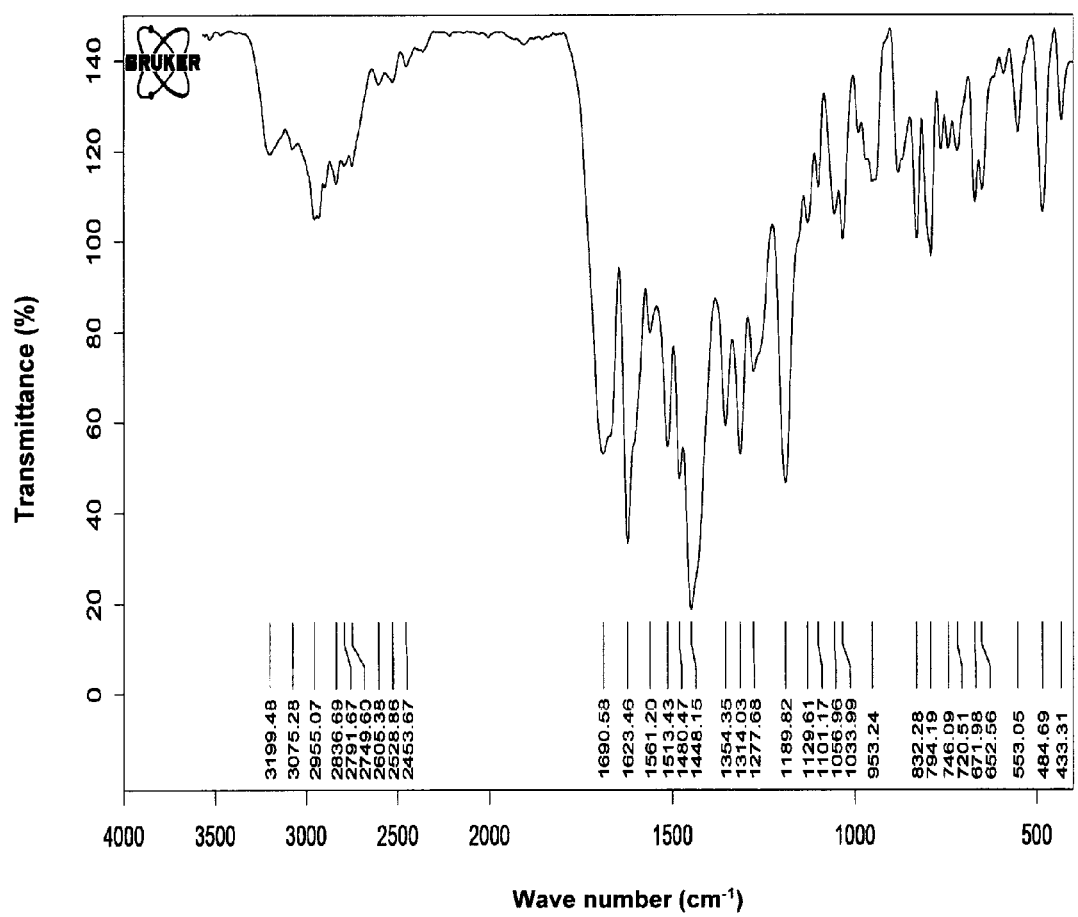
Figure 9:
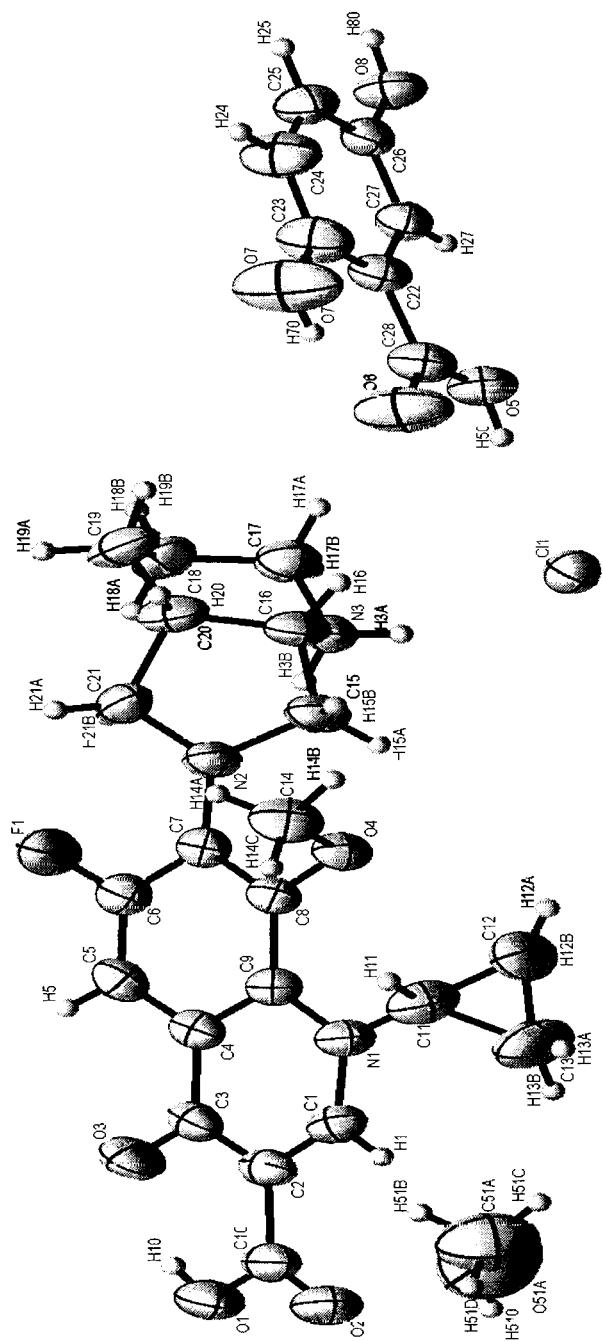

FIGS. 7, 8 and 9 show the DSC-TGA thermal analysis, the TF-IR infrared spectrum and the asymmetric unit of the crystalline structure of Moxifloxacin HCl co-crystal with 2,5-dihydroxybenzoic acid.

Figure 14:
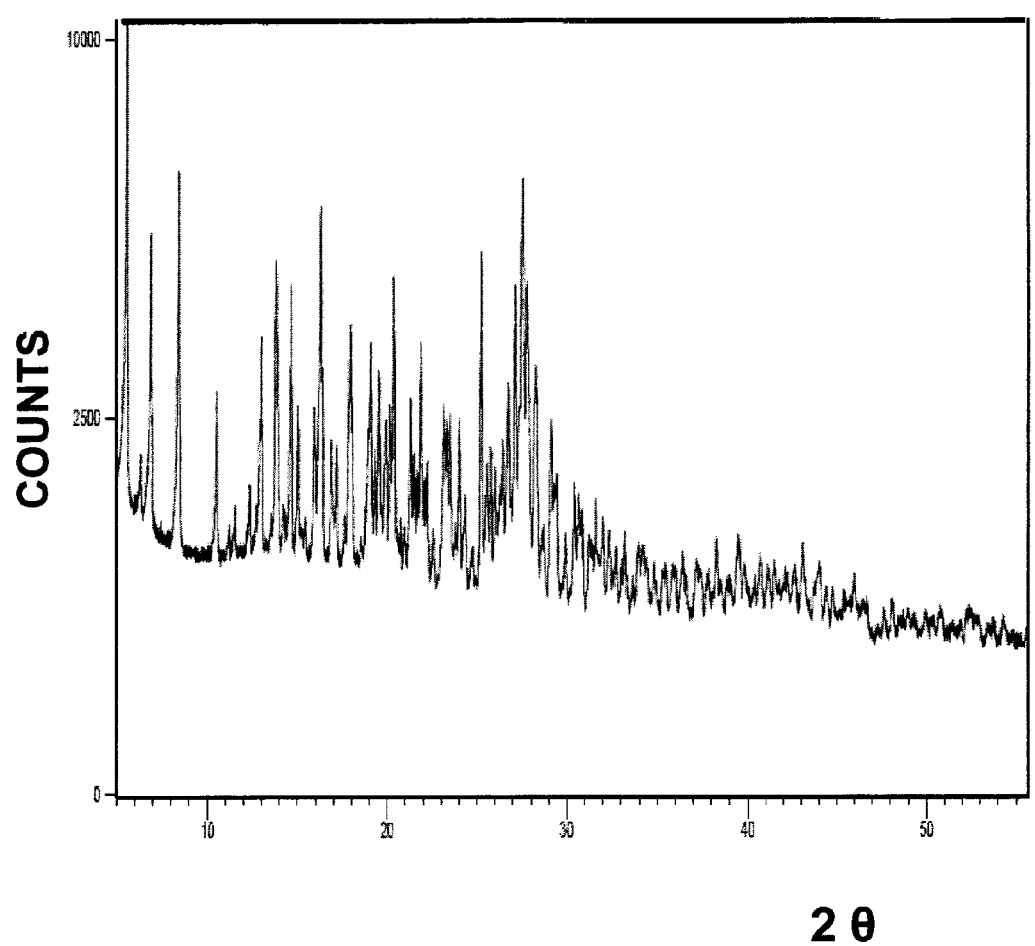
Figure 15:
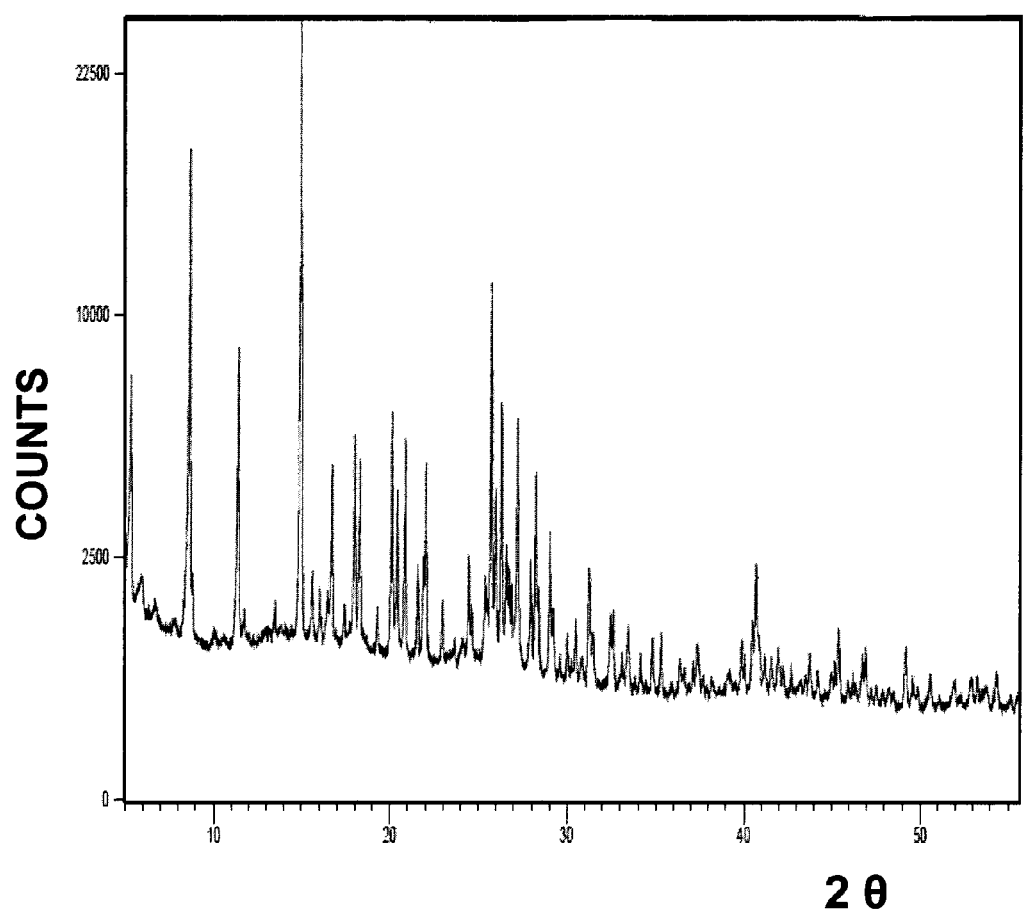
Figure 16:
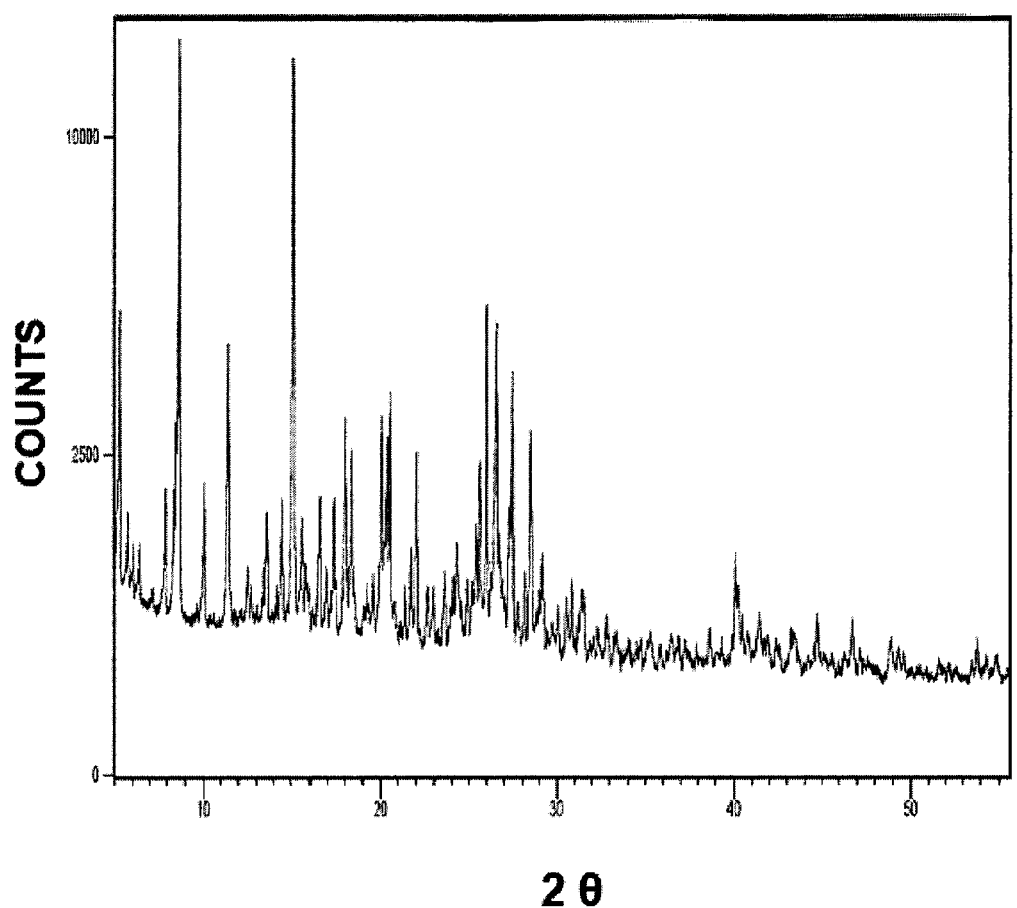
Figure 17:
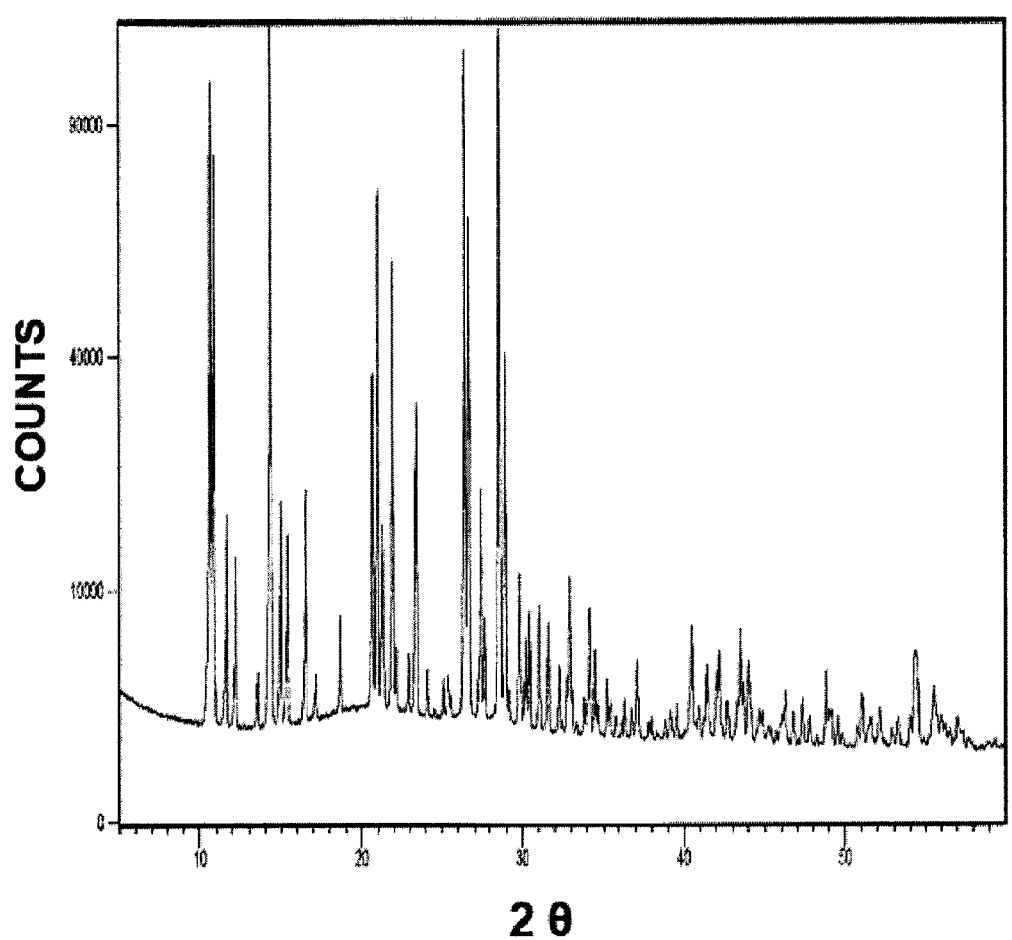
Figure 18:
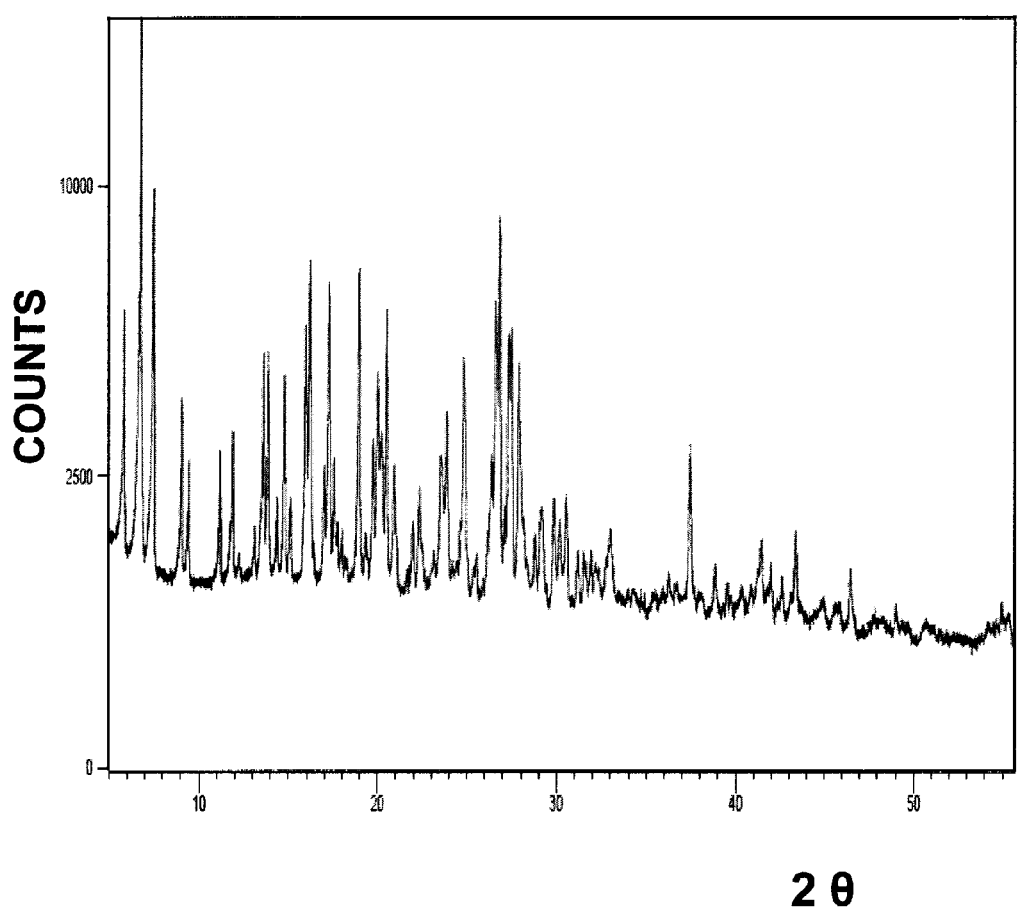
Figure 19:
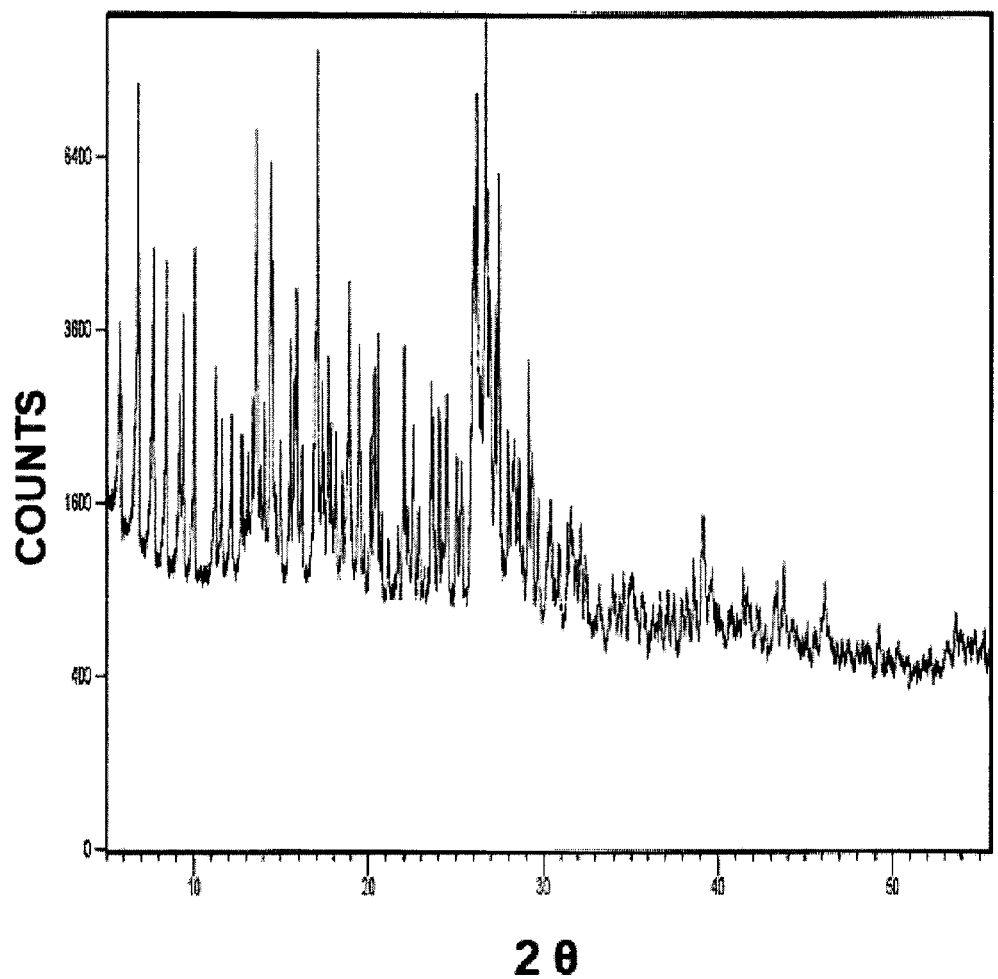

In the crystallization of saturated solutions in THF in the case of gallic acid, the diffraction pattern corresponds to the one of moxifloxacin HCl, whereas for the 3,5-dihydroxybenzoic acid a NSF with a high degree of amorphicity was obtained. When the crystallization of saturated solutions was carried out in methanol, the powder diffraction pattern obtained showed an NSF either for both gallic acid (FIG. 14) and 3,5-dihydroxybenzoic acid (FIG. 13). Resorcinol also generated a co-crystal (FIG. 16), as well as glycolic acid (FIG. 17), DL-malic acid (FIG. 18) and D-tartaric acid (FIG. 19).

Figure 20:
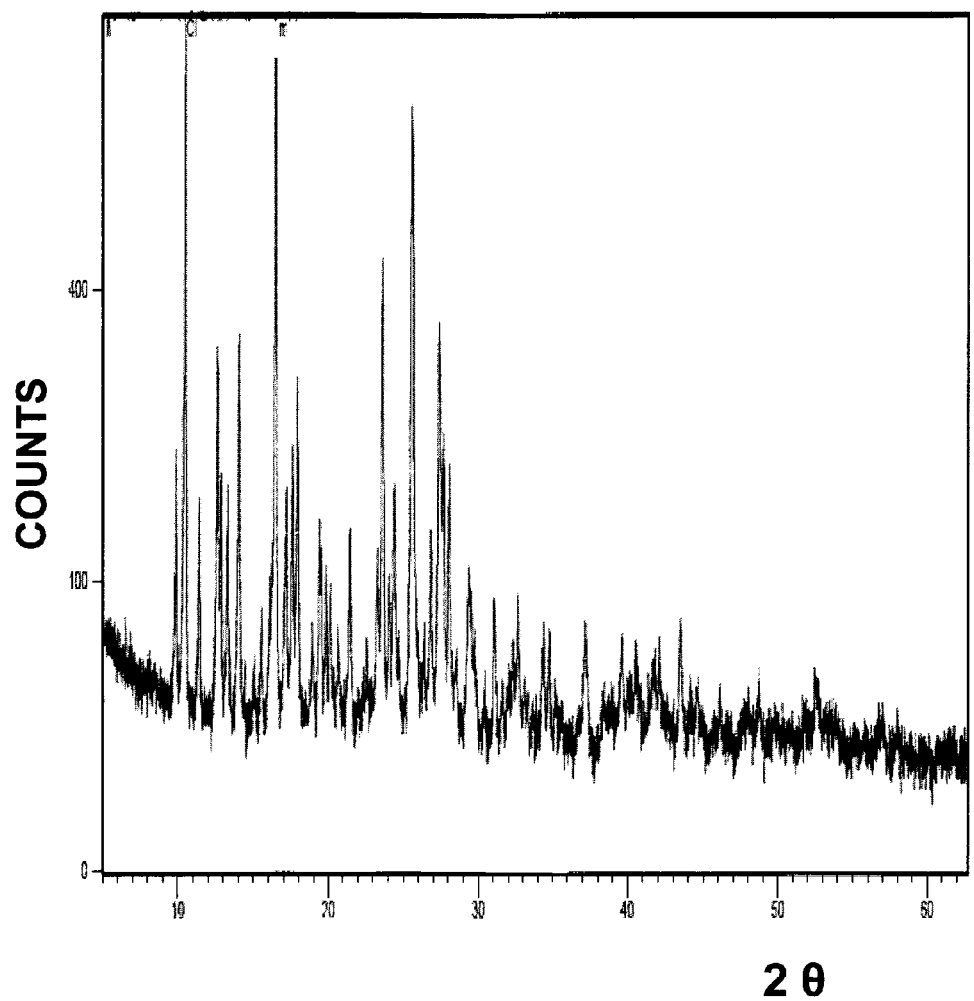
Figure 21:
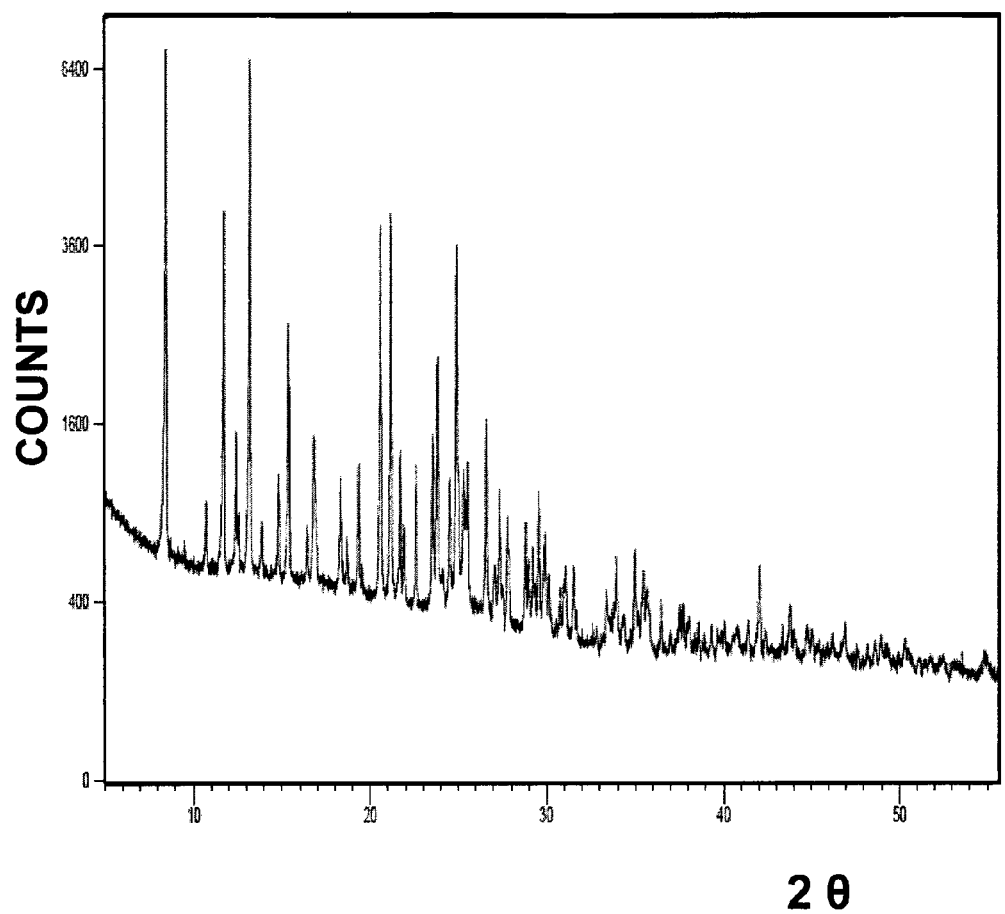
Figure 22:
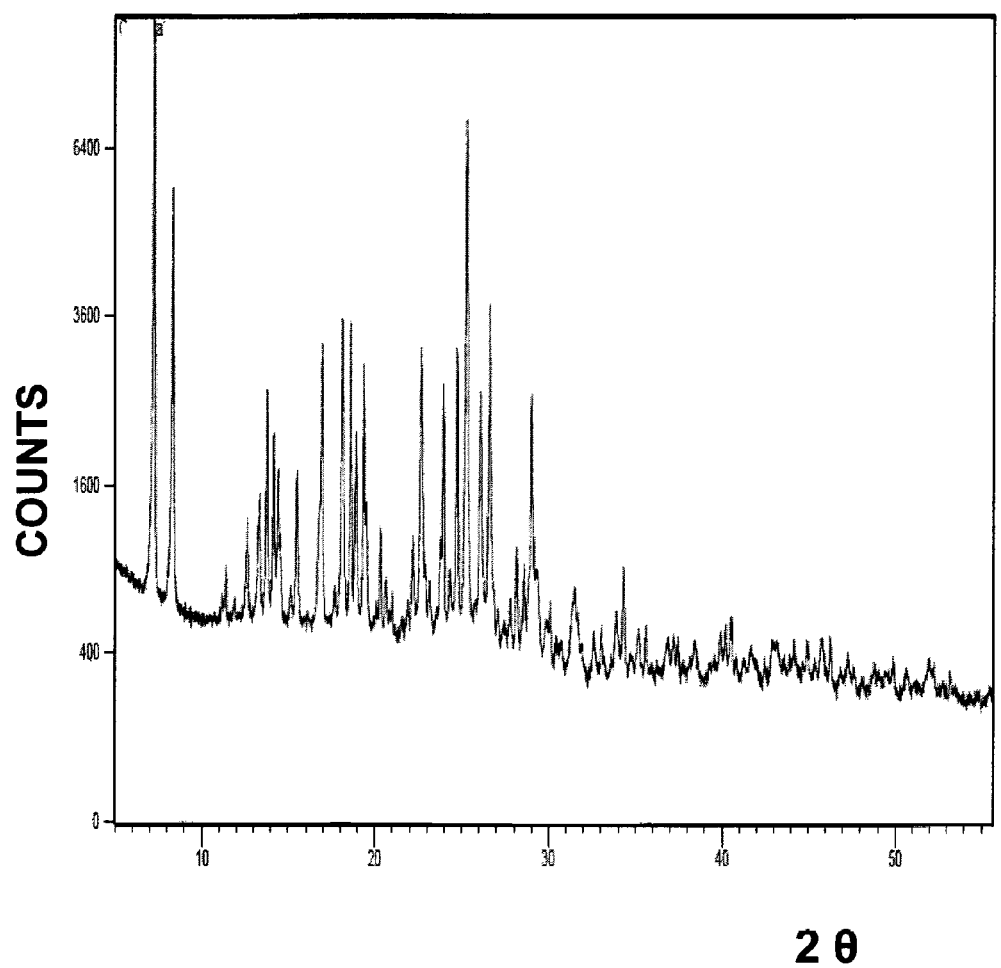

Crystallizations with aromatic hydroxibenzamides also showed positive results. The X-ray powder diffraction pattern analysis corresponding to 4-hydroxybenzamide in THF shows the formation of a new phase (FIG. 20). Crystallization of saturated solutions of 4-aminobenzoic acid in methanol also generated a co-crystal (FIG. 21), as well as with 4-hydroxybenzyl alcohol (FIG. 22).

Figure 23:
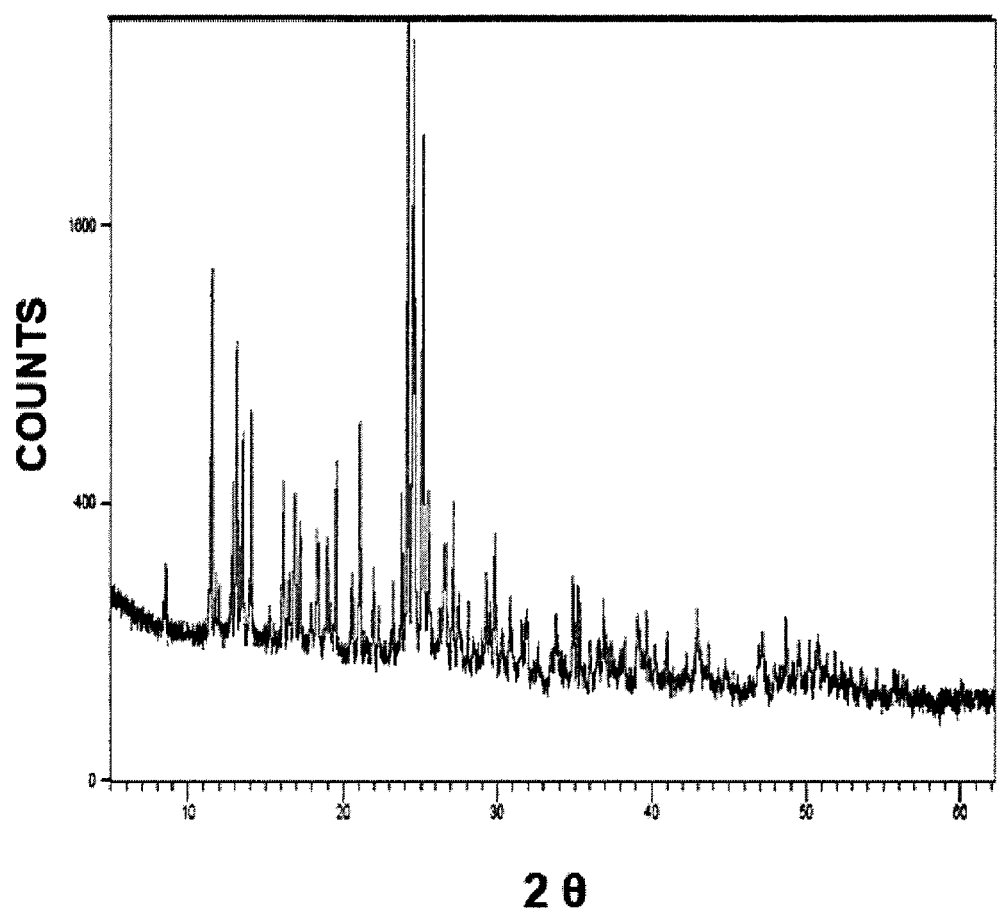
FIGS. 23-32 illustrate the results of the characterization of the ciprofloxacin co-crystals obtained in the present invention.
Figure 24:
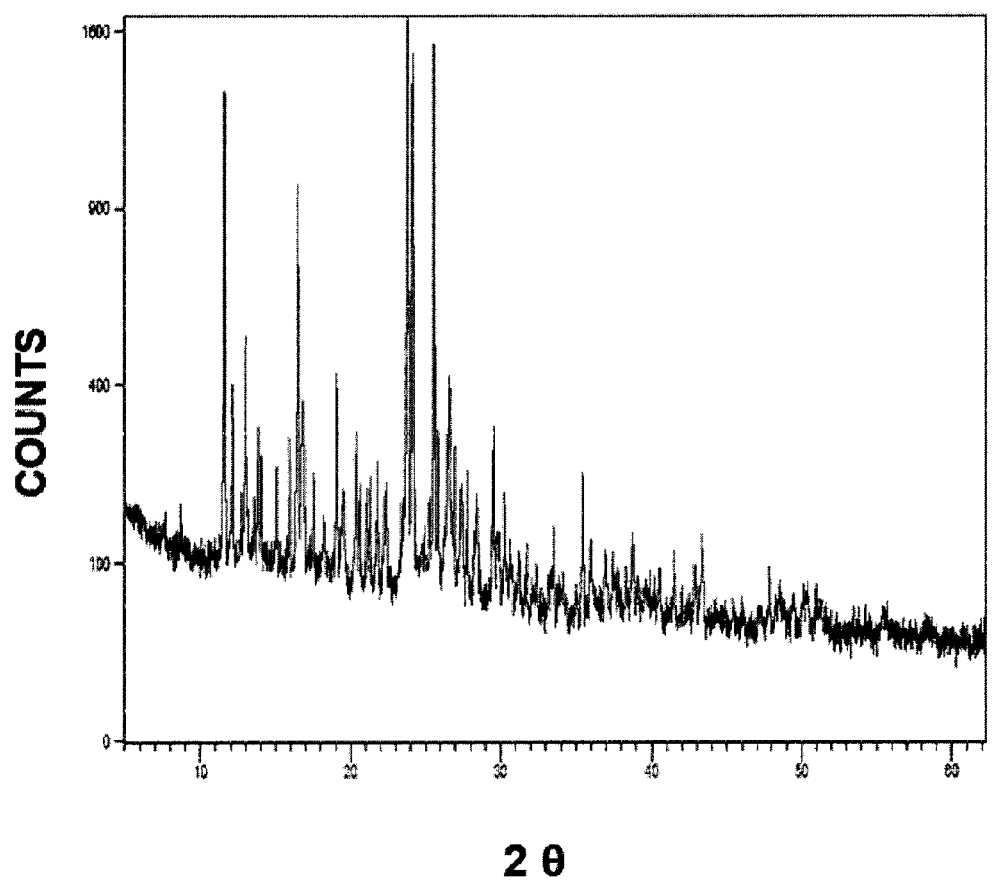
Figure 25:
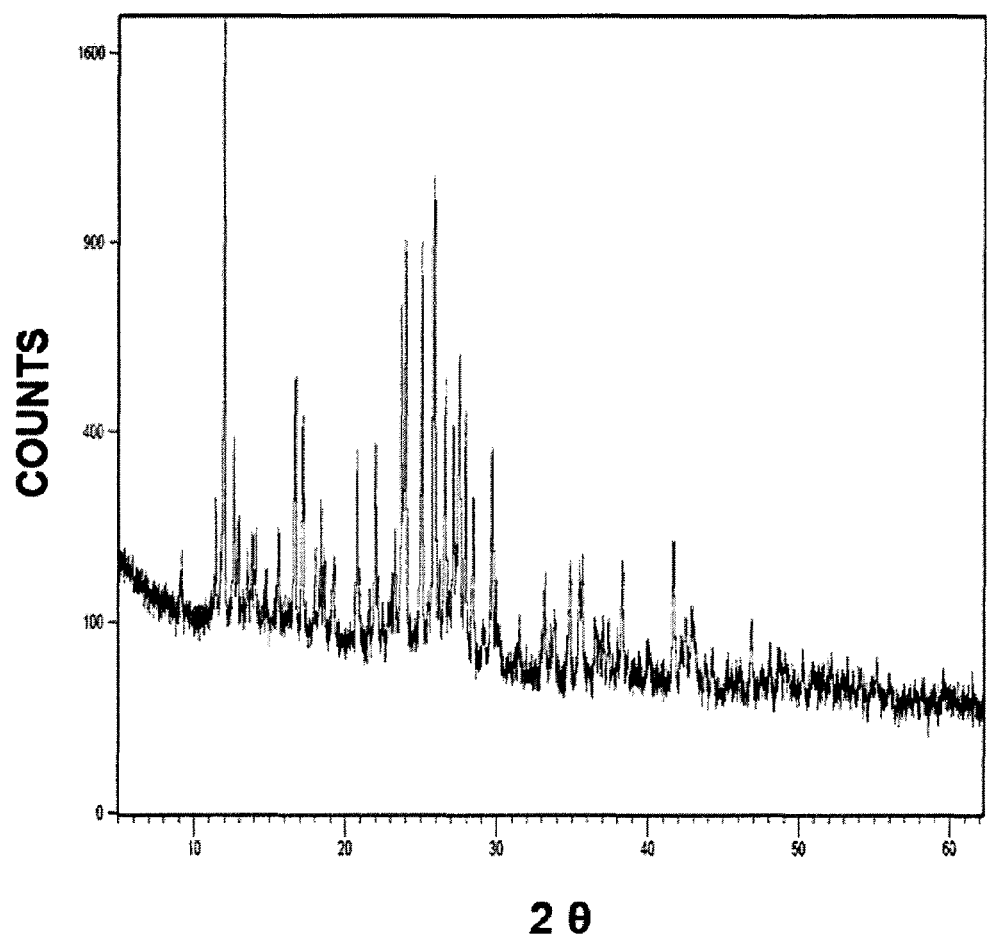
Figure 26:
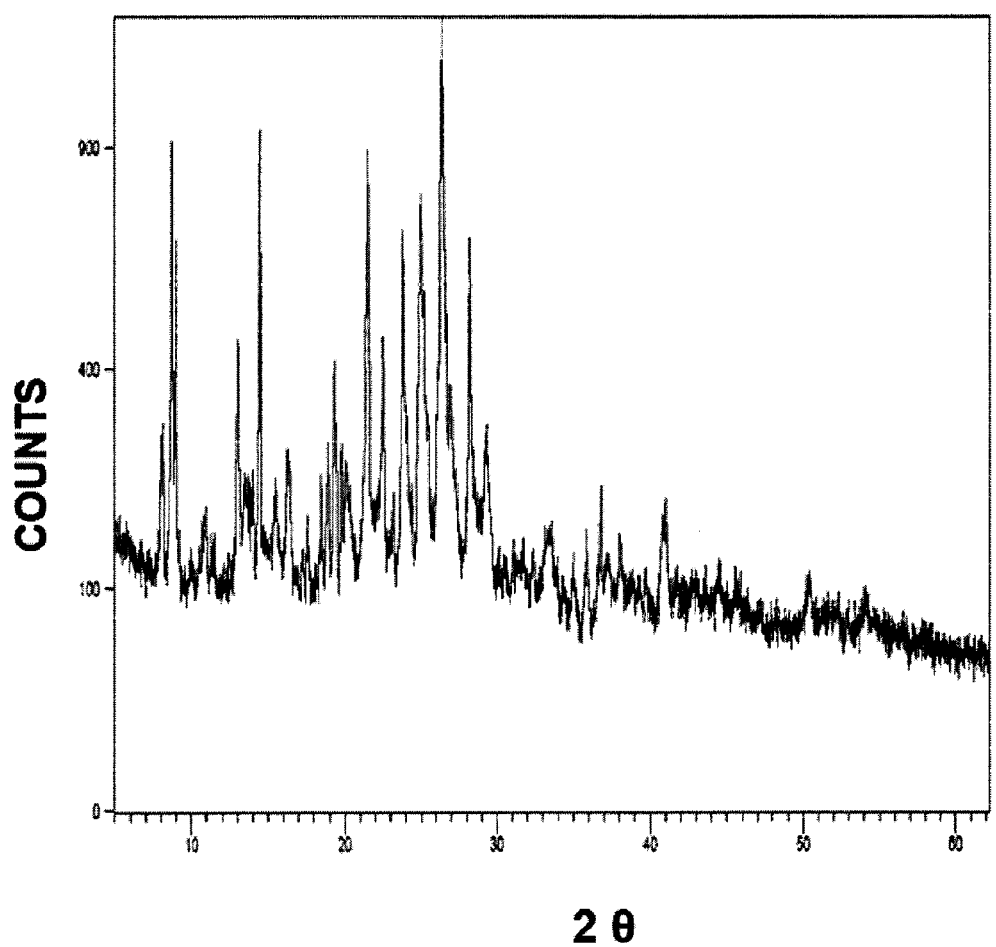
Figure 27:
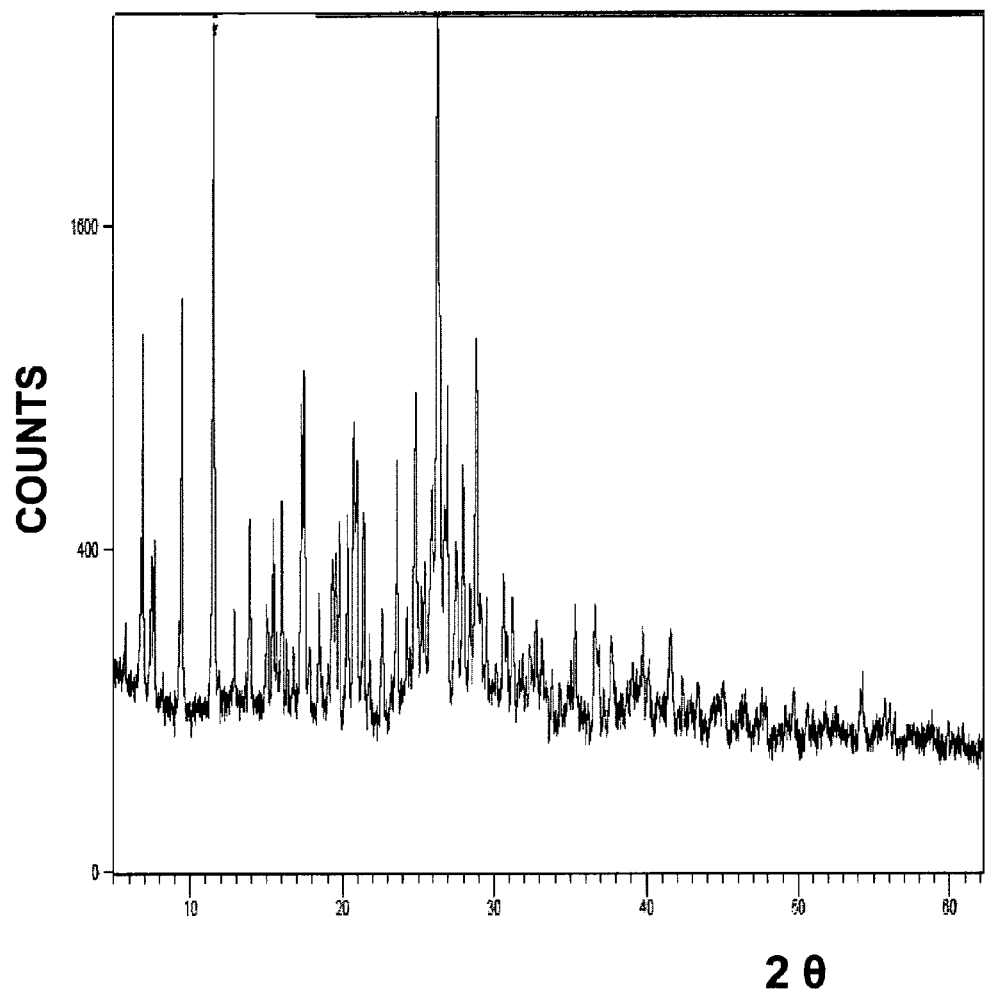
Figure 28:
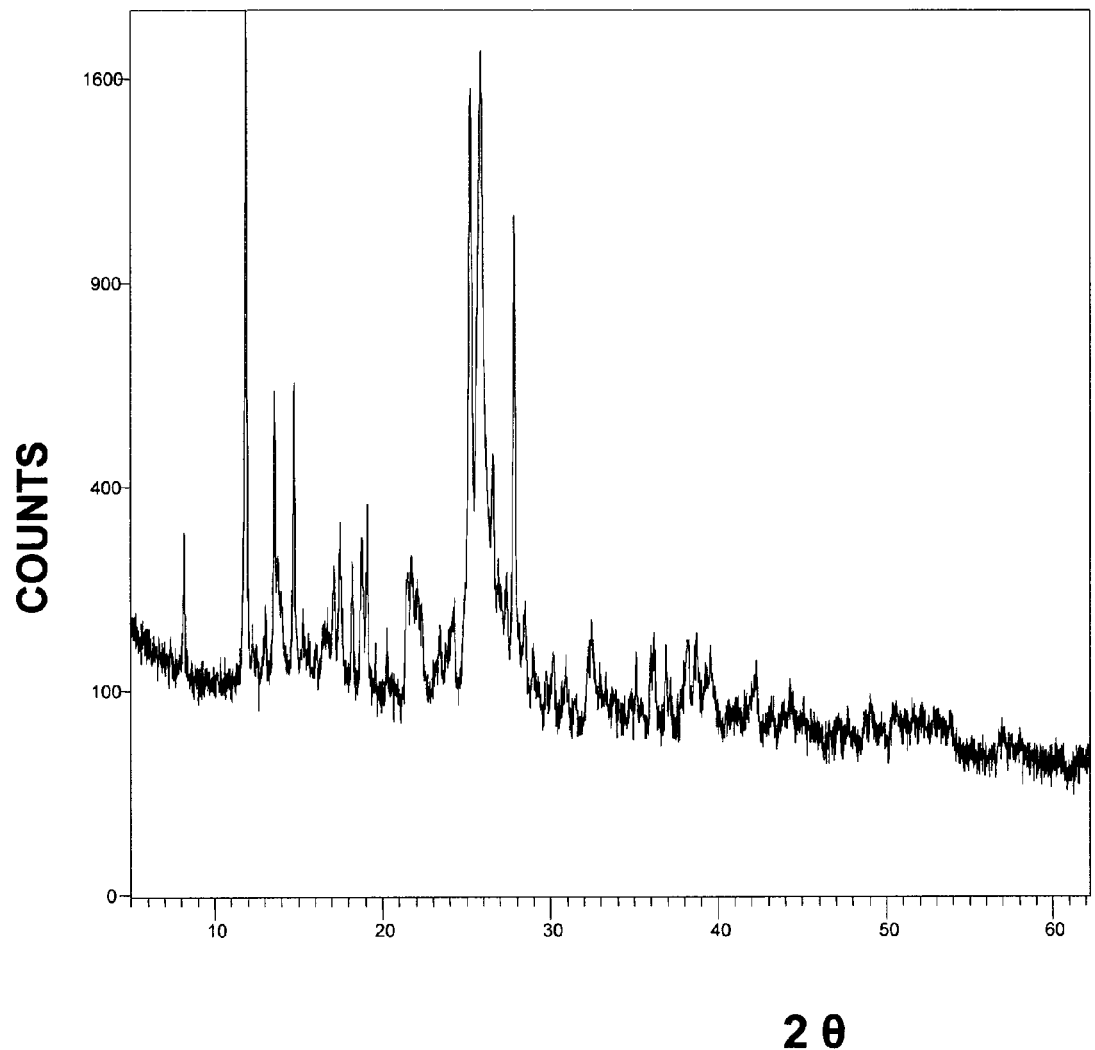
Figure 29:
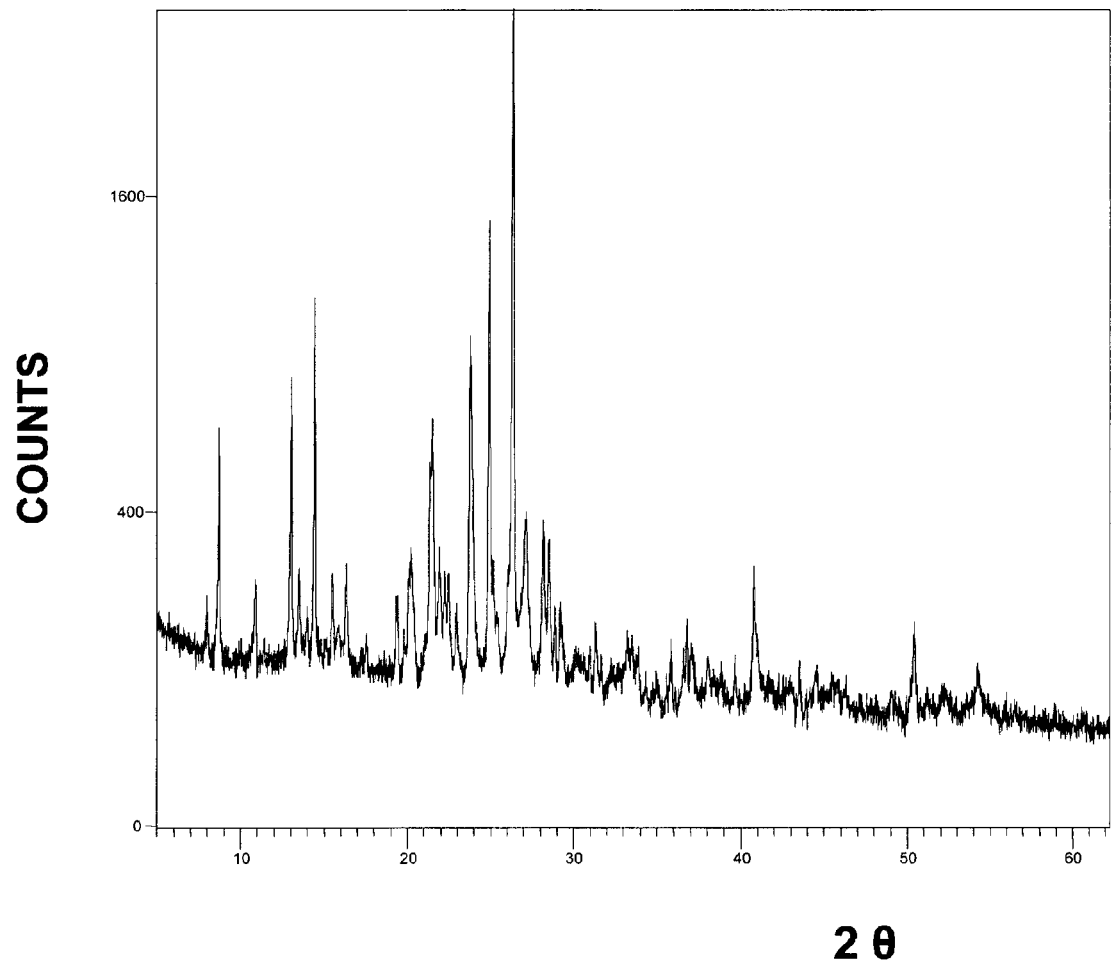
Figure 30:
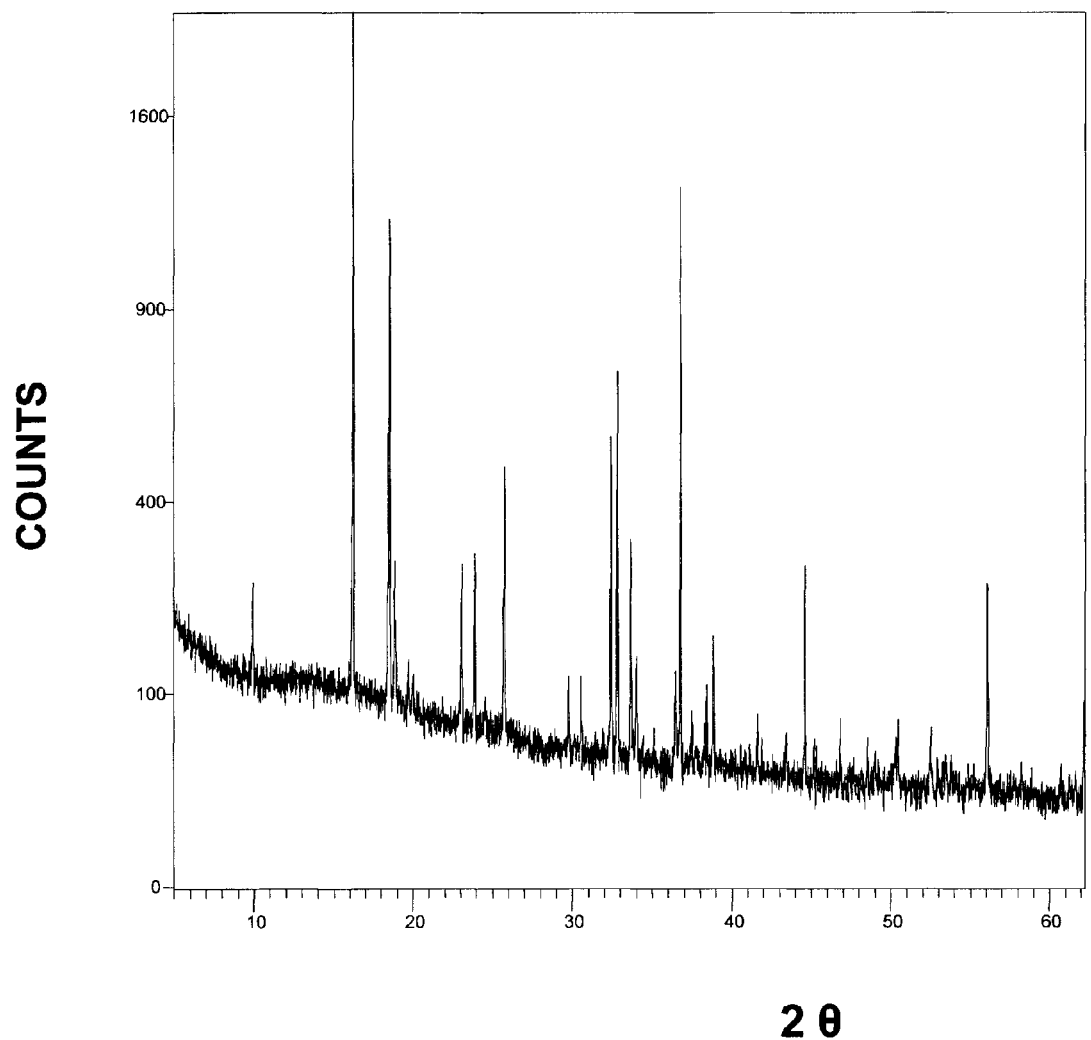
Figure 31:
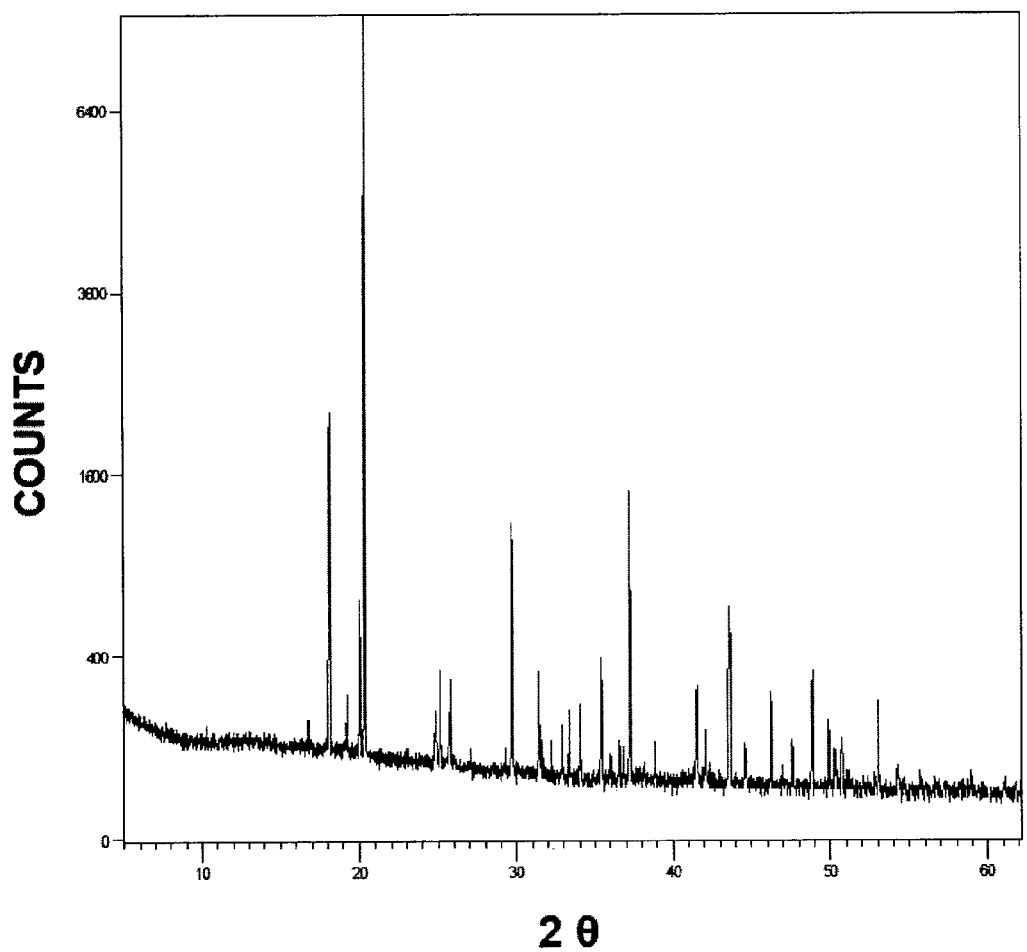
Figure 32:
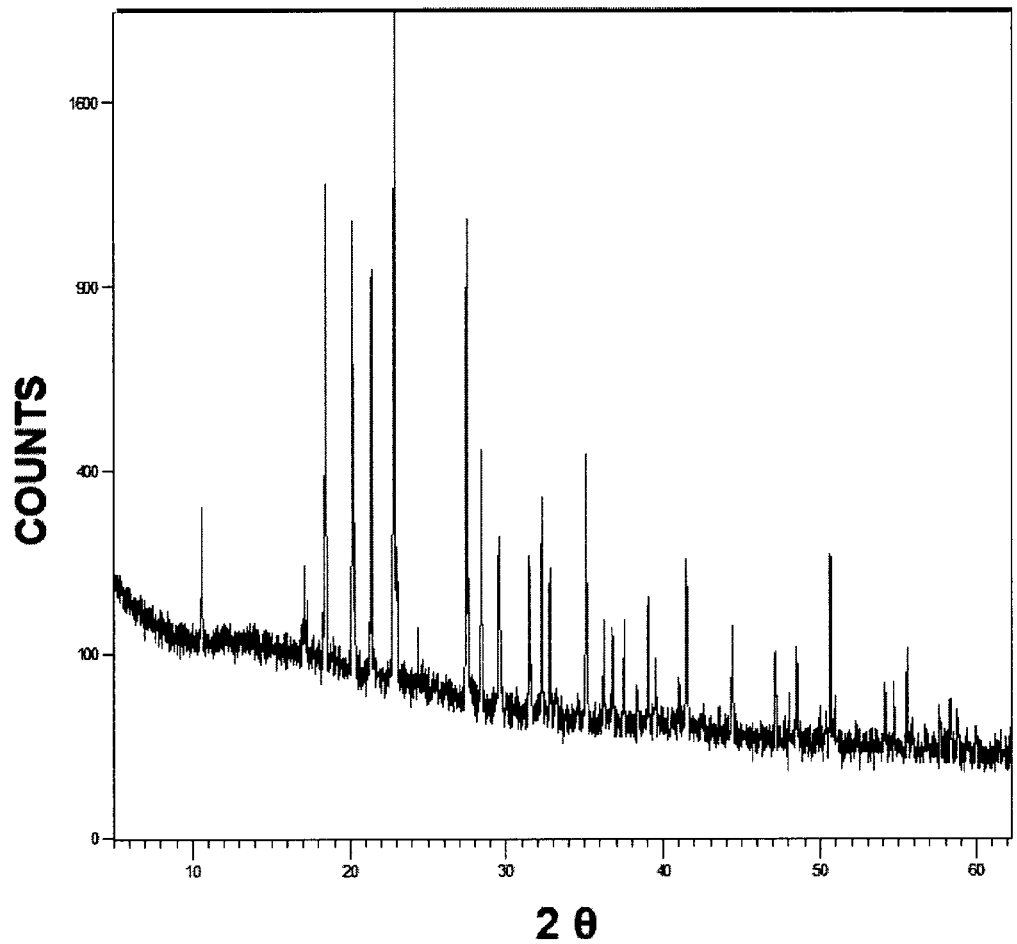

Crystallizations between ciprofloxacin HCl and 4-hydroxybenzoic acid resulted in stable NSF, characterized by an X-ray diffraction pattern different to the one of the starting materials (FIG. 23). When employing combinations with other hydroxycarboxylic acids or aromatic polyols, NSF were generated. For example, NSF were obtained from ciprofloxacin hydrochloride in combination with the co-formers 3-hydroxybenzoic acid (FIG. 24), 2,3-dihydroxybenzoic acid (FIG. 25), 2,4-dihydroxybenzoic acid (FIG. 26), 2,5-dihydroxybenzoic acid (FIG. 27), 3,4-dihydroxybenzoic acid (FIG. 28), 3,5-dihydroxybenzoic acid (FIG. 29), cathecol (FIG. 30), resorcinol (FIG. 31) or hydroquinone (FIG. 32).

New Solid Phases Obtained (NSP)

In the preferred embodiment of the present invention, as a result of experimentation NSF of moxifloxacin and ciprofloxacin were obtained. Some examples are shown hereinbelow.

The combination of the moxifloxacin salt with a chemical compound of aliphatic hydroxycarboxylic acids such as glycolic acid, D-tartaric acid or malic acid, among others.

The combination of the moxifloxacin salt with a chemical compound of derivatives of hydroxycarboxylic acids and aromatic analogs such as 3-hydroxybenzoic acid, 4-hydroxybenzoic acid, 2,5-dihydroxybenzoic acid, 3,4-dihydroxybenzoic acid, 3,5-dihydroxybenzoic acid, gallic acid, 2,4-dihydroxybenzoic acid, 4-hydroxybenzamide, 4-aminobenzoic acid and others.

The combination of the moxifloxacin salt with a chemical compound of the aromatic polyol kind, such as cathecol, resorcinol or 4-hydroxybenzyl alcohol, among others.

The combination of the moxifloxacin salt with a chemical compound of a derivative of hydroxycarboxylic acids and aromatic analogues such as 3-hydroxybenzoic acid, 4-hydroxybenzoic acid, 2,5-dihydroxybenzoic acid, 3,4-dihydroxybenzoic acid, 3,5-dihydroxybenzoic acid 2,4-dihydroxybenzoic acid, 2,3-dihydroxybenzoic among others.

The combination of the moxifloxacin salt with a chemical compound of the aromatic polyol kind, such as cathecol, resorcinol or hydroquinone, among others.

The ciprofloxacin and moxifloxacin NSF obtention process can additionally start from a salt different from the hydrochloride salt, where the chlorine can be substituted by another halogen. The selected moxifloxacin salt is combined with any of the aforementioned co-formers.

What is claimed is:

1. A moxifloxacin co-crystal of formula:

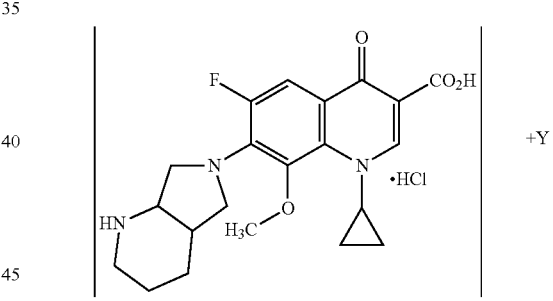

Wherein:

Y is selected from the group consisting of: 3-hydroxybenzoic acid, 4-hydroxybenzoic acid, 2,4-dihydroxybenzoic acid, 2,5-dihydroxybenzoic acid, 3,4-dihydroxybenzoic acid, 3,5-dihydroxybenzoic acid, glycolic acid, DL-malic acid, 4-hydroxybenzamide, catechol, 4-aminobenzoic acid, resorcinol and 4-hydroxybenzyl alcohol; or a solvate or a hydrate thereof.

2. A co-crystal in accordance with claim 1, wherein Y is 4-hydroxybenzoic acid; or a solvate or a hydrate thereof.

3. A co-crystal in accordance with claim 1, wherein Y is 2,5-dihydroxybenzoic acid; or a solvate or a hydrate thereof.

4. A co-crystal in accordance with claim 1, wherein Y is 3-hydroxybenzoic acid; a solvate or a hydrate thereof.

5. A co-crystal in accordance with claim 1, wherein Y is 2,4-dihydroxybenzoic acid; or a solvate or a hydrate thereof.

6. A co-crystal in accordance with claim 1, wherein Y is 3,4-dihydroxybenzoic acid; or a solvate or a hydrate thereof.

7. A co-crystal in accordance with claim 1, wherein Y is 3,5-dihydroxybenzoic acid; or a solvate or a hydrate thereof.

8. A co-crystal in accordance with claim 1, wherein Y is catechol; or a solvate or a hydrate thereof.

9. A co-crystal in accordance with claim 1, wherein Y is resorcinol; or a solvate or a hydrate thereof.

10. A co-crystal in accordance with claim 1, wherein Y is glycolic acid; or a solvate or a hydrate thereof.

11. A co-crystal in accordance with claim 1, wherein Y is DL-malic acid; or a solvate or a hydrate thereof.

12. A co-crystal in accordance with claim 1, wherein Y is 4-hydroxybenzamide; or a solvate or a hydrate thereof.

13. A co-crystal in accordance with claim 1, wherein Y is 4-aminobenzoic acid; or a solvate or a hydrate thereof.

14. A co-crystal in accordance with claim 1, wherein Y is 4-hydroxybenzyl alcohol; or a solvate or a hydrate thereof.

15. A ciprofloxacin co-crystal of formula:

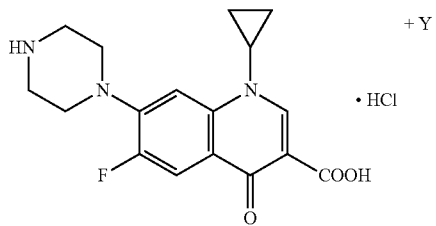

wherein:
Y is selected from the group consisting of: 3-hydroxybenzoic acid, 4-hydroxybenzoic acid, 2,5-dihydroxybenzoic acid, 3,4-dihydroxybenzoic acid, 3,5-dihydroxybenzoic acid, 2,4-dihydroxybenzoic acid, 2,3-dihydroxybenzoic acid, catechol, resorcinol and hydroquinone;
or a solvate or a hydrate thereof.

16. A co-crystal in accordance with claim 15, wherein Y is 3-hydroxybenzoic acid; or a solvate or a hydrate thereof.

17. A co-crystal in accordance with claim 15, wherein Y is 4-hydroxybenzoic acid; or a solvate or a hydrate thereof.

18. A co-crystal in accordance with claim 15, wherein Y is 2,4-dihydroxybenzoic acid; or a solvate or a hydrate thereof.

19. A co-crystal in accordance with claim 15, wherein Y is 3,4-dihydroxybenzoic acid; or a solvate or a hydrate thereof.

20. A co-crystal in accordance with claim 15, wherein Y is 2,5-dihydroxybenzoic acid; or a solvate or a hydrate thereof.

21. A co-crystal in accordance with claim 15, wherein Y is 2,3-dihydroxybenzoic acid; or a solvate or a hydrate thereof.

22. A co-crystal in accordance with claim 15, wherein Y is 3,5-dihydroxybenzoic acid; or a solvate or a hydrate thereof.

23. A co-crystal in accordance with claim 15, wherein Y is catechol; or a solvate or a hydrate thereof.

24. A co-crystal in accordance with claim 15, wherein Y is resorcinol; or a solvate or a hydrate thereof.

25. A co-crystal in accordance with claim 15, wherein Y is hydroquinone; or a solvate or a hydrate thereof.

26. A method for treating a bacterial infection comprising administering to a patient an effective amount of the moxifloxacin co-crystal of claim 1.

27. A method for treating a bacterial infection comprising administering to a patient an effective amount of the ciprofloxacin co-crystal of claim 15.

* * * * *